US010118934B2

(12) United States Patent
Kiessling et al.

(10) Patent No.: US 10,118,934 B2
(45) Date of Patent: Nov. 6, 2018

(54) INHIBITORS OF UDP-GALACTOPYRANOSE MUTASE

(71) Applicants: Wisconsin Alumni Research Foundation, Madison, WI (US); The Regents of the University of California, Oakland, CA (US)

(72) Inventors: Laura L. Kiessling, Madison, WI (US); Virginia A. Kincaid, Madison, WI (US); Nir London, Rehovot (IL); Brian K. Shoichet, Kentfield, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/622,972

(22) Filed: Jun. 14, 2017

(65) Prior Publication Data

US 2017/0283437 A1   Oct. 5, 2017

Related U.S. Application Data

(62) Division of application No. 14/728,914, filed on Jun. 2, 2015, now Pat. No. 9,708,344.

(60) Provisional application No. 62/007,355, filed on Jun. 3, 2014.

(51) Int. Cl.
  *C07D 417/04*   (2006.01)
  *C07D 513/04*   (2006.01)

(52) U.S. Cl.
  CPC ......... *C07D 513/04* (2013.01); *C07D 417/04* (2013.01)

(58) Field of Classification Search
  CPC .................................................. C07D 417/04
  See application file for complete search history.

(56) References Cited

U.S. PATENT DOCUMENTS

| 8,273,778 B2 | 9/2012 | Kiessling et al. |
| 2005/0222408 A1 | 10/2005 | Lee et al. |
| 2005/0261294 A1 | 11/2005 | Mjalli et al. |

FOREIGN PATENT DOCUMENTS

| WO | WO 2005/007625 | 1/2005 |
| WO | WO 2009/089027 | 7/2009 |

OTHER PUBLICATIONS

Lack et al. Journal of Medicinal Chemistry (2011), 54(24), 8563-8573.*
Aytac et al. (2009) "Synthesis of 3,6-disubstituted 7H-1,2,4-triazolo[3,4-b]-1,3,4-thiadiazines as novel analgesic/anti-inflammatory compounds," European Journal of Medicinal Chemistry. 44(11):4528-4538.
Beis et al (2005) "Crystal Structures of *Mycobacteria tuberculosis* and Klebsiella pneumoniae UDP-Galactopyranose Mutase in the Oxidised State and Klebsiella pneumoniae UDP-Galactopyranose Mutase in the (Active) Reduced State," J. Mol. Biol. 348(4):971-982.
Borrelli et al. (2010) "Antimycobacterial activity of UDP-galactopyranose mutase inhibitors," Int. J. Antimicrob. Agents. 36(4):364-368.
Caravano et al. (2003) "Synthesis and inhibition properties of conformational probes for the mutase-catalyzed UDP-galactopyranose/furanose interconversion," Chem.—Eur. J. 9:5888-5898.
Caravano et al. (2004) "Efficient synthesis of a nucleoside-diphospho-exo-glycal displaying time-dependent inactivation of UDP-galactopyranose mutase," Chem. Commun. 2004(10):1216-1217.
Caravano et al. (2006) "A new methodology for the synthesis of fluorinated exo-glycals and their time-dependent inhibition of UDP-galactopyranose mutase," Chem.—Eur. J. 12:3114-3123.
Carlson et al. (2006) "Chemical probes of UDP-galactopyranose mutase," Chem. Biol. 13(8):825-837.
Chad et al. (2007) "Site-directed mutagenesis of UDP-galactopyranose mutase reveals a critical role for the active-site, conserved arginine residues," Biochemistry. 46(23):6723-6732.
Dhindsa et al. (1986) "Synthesis and mass spectral studies of some 3-alkyl-6-aryl-7-carbethoxy/carboxy-methyl-s-triazolo[3,4-b][1,3,4]thiadiazines," Indian Journal of Chemistry, Section B: Organic Chemistry Including Medicinal Chemistry. 25B(3):283-287.
Dykhuizen et al. (2008) "Inhibitors of UDP-galactopyranose mutase thwart mycobacterial growth," J. Am. Chem. Soc. 130(21):6706-6707.
Dykhuizen et al. (2009) "Potent ligands for prokaryotic UDP-galactopyranose mutase that exploit an enzyme subsite," Org. Lett. 11(1):193-196.
El-Serwy et al. (Sep. 6, 2012) "Synthesis and anti-inflammatory properties of novel 1,2,4-triazole derivatives," Res. Chem. Intermed. 39:2543-2554.
Gaulton et al. (Sep. 23, 2011) "ChEMBL: a large-scale bioactivity database for drug discovery," Nucleic Acids Res. 40(Database Issue):D1100-D1107.
Ghavami et al. (2004) "Synthesis of a novel class of sulfonium ions as potential inhibitors of UDP-galactopyranose mutase," Carbohydr. Res. 339:401-407.

(Continued)

*Primary Examiner* — Kahsay Habte
(74) *Attorney, Agent, or Firm* — Leydig, Voit & Mayer, Ltd

(57) ABSTRACT

Compounds and salts thereof which inhibit microbial growth or attenuate the virulence of pathogenic microorganisms and which inhibit UDP-galactopyranose mutase (UGM). Compounds of the invention include triazolothiadiazines, particularly 3, 6, 7-substituted-7H-[1,2,4]triazolo[3,4-b][1,3,4]thiadiazines, and 4-(1H-pyrrol-3-yl) thiazoles, particularly 4-(1,2,5-substituted-1H-pyrrol-3-yl)-2-substituted thiazoles, and salts thereof. Methods for inhibiting growth or attenuating virulence of microbial pathogens including mycobacterium, for example, *M. tuberculosis* and *M. smegmatis* and *Klebsiella*, for example, *Klebsiella pneumoniae*. Methods for inhibiting eukaryotic human and animal pathogens, and fungi and nematodes in particular. Methods for treatment of infections by prokaryotic and eukaryotic pathogens employing compounds of the invention.

19 Claims, 26 Drawing Sheets

(56) References Cited

OTHER PUBLICATIONS

Ghose et al. (1999) "A Knowledge-Based Approach in Designing Combinatorial or Medicinal Chemistry Libraries for Drug Discovery," J. Combin. Chem. 1:55-68.
Gruber et al. (2009) "Ligand Binding and Substrate Discrimination by UDP-Galactopyranose Mutase," J. Mol. Biol. 391(2):327-340.
Gruber et al. (2009) "X-ray crystallography reveals a reduced substrate complex of UDP-galactopyranose mutase poised for covalent catalysis by flavin," Biochemistry. 48(39):9171-9173.
Itoh et al. (2007) "Synthesis and analysis of substrate analogues for UDP-galactopyranose mutase: implication for an oxocarbenium ion intermediate in the catalytic mechanism," Org. Lett. 9:879-882.
Jakhar et al. (Jan. 2012) "Molecular iodine mediated one step synthesis and antibacterial properties of some 3-aryl-6-(6-substituted-4-methylcinnolin-3-yl)-7H-1,2,4-triazolo[3,4-b][1,3,4]thiadiazines," Indian Journal of Chemistry, Section B: Organic Chemistry Including Medicinal Chemistry. 51B(1):313-317.
Kincaid et al. (Aug. 17, 2015) "Virtual Screening for UDP-Galactopyranose Mutase Ligands Identifies a New Class of Antimycobacterial Agents," ACS Chem. Biol. 10(10):2209-2218.
Lee et al. (1997) "Inhibition of UDP-Gal Mutase and Mycobacterial Galactan Biosynthesis by Pyrrolidine Analogues of Galactofuranose," Tetrahedron Lett. 38:6733-6736.
Lee et al. (1999) "An approach to combinatorial library generation of galactofuranose mimics as potential inhibitors of mycobacterial cell wall biosynthesis: Synthesis of a peptidomimetic of uridine 5'-diphosphogalactofuranose (UDP-Galf)," Tetrahedron Lett. 40:8689-8692.
Liautard et al. (2006) "Diastereoselective synthesis of novel iminosugar-containing UDP-Galf mimics: potential inhibitors of UDP-Gal mutase and UDP-Galf transferases," J. Org. Chem. 71:7337-7345.
Liautard et al. (2006) "Stereoselective synthesis of alpha-C-Substituted 1,4-dideoxy-1,4-imino-D-galactitols. Toward original UDP-Galf mimics via cross-metathesis," Org. Lett. 8:1299-1302.
Magnet et al. (2010) "Leads for antitubercular compounds from kinase inhibitor library screens," Tuberculosis 90:354-360.
Mazzone et al. (1989) "Carboxymethyl- and carboxy-derivatives of 7H- and 5H-1,2,4-triazolo[3,4-b][1,3,4]thiadiazine: Synthesis and biological evaluation," Farmaco. 44(10):933-44.
McGovern et al. (2002) "A common mechanism underlying promiscuous inhibitors from virtual and high-throughput screening," J. Med. Chem. 45(8):1712-1722.
Owen et al. (Jun. 8, 2012) "Colloidal aggregation affects the efficacy of anticancer drugs in cell culture," ACS Chem. Biol. 7(8):1429-1435.
Pan et al. (2001) "Cell Wall Core Galactofuran Synthesis Is Essential for Growth of *Mycobacteria*," J. Bacteriol. 183(13):3991-3998.
Pan et al. (2007) "Synthesis of acyclic galactitol- and lyxitol-aminophosphonates as inhibitors of UDP-galactopyranose mutase," Tetrahedron Lett. 48:4353-4356.
Pedersen et al. (2003) "Galactofuranose metabolism: a potential target for antimicrobial chemotherapy," J. Cell. Mol. Life Sci. 60:259-266.
Soltero-Higgin et al. (2004) "A unique catalytic mechanism for UDP-galactopyranose mutase," Nat. Struct. Mol. Biol. 11(6):539-543.
Soltero-Higgin et al. (2004) "Identification of inhibitors for UDP-galactopyranose mutase," J. Am. Chem. Soc. 126(34):10532-10533.
Tangallapally et al. (2004) "Synthesis and evaluation of nitrofuranylamides as novel antituberculosis agents," J. Med. Chem. 47:5276-5283.
Teague et al. (1999) "The Design of Leadlike Combinatorial Libraries," Angew. Chem. Int. Ed. Engl. 38(24):3743-3748.
Veerapen et al. (2004) "Synthesis of novel ammonium and selenonium ions and their evaluation as inhibitors of UDP-galactopyranose mutase," Carbohydr. Res. 339:2205-2217.
Vovk et al. (2010) "Synthesis of 1-(4-trifluoromethoxyphenyl)-2,5-dimethyl-3-(2-R-thiazol-4-yl)-1H-pyrroles via chain heterocyclization," Molecules. 15:997-1006.
Wesener et al. (Jun. 11, 2013) "UDP-galactopyranose mutase in nematodes," Biochemistry. 52(25):4391-4398.
Westphal et al. Zeitschrift fuer Chemie (1969), 9(3), 111-12.

* cited by examiner

| # | R₁ | R₂ | % inhibition 100μM | % inhibition 50μM |
|---|---|---|---|---|
| 6 | furan-CH | phenyl-CH | 33.8 ± 3.2 | 24.9 ± 3.6 |
| First generation analogs | | | | |
| 16 | furan-CH | 4-F-phenyl-CH | 37.6 ± 2.0 | 39.2 ± 3.9 |
| 17 | cyclopropyl | phenyl-CH | 8.9 ± 0.4 | 16.2 ± 0.7 |
| 18 | 4-F-phenyl-CH | phenyl-CH | 74.1 ± 2.8 | 59.5 ± 9.3 |
| 19 | 4-F-phenyl-CH₂CH | phenyl-CH | 91.5 ± 0.0 | 78.0 ± 0.7 |
| 20 | furan-CH | furan-CH | 46.1 ± 0.5 | 47.9 ± 11.0 |
| 21 | H-CH | 4-O-phenyl-CH | 71.7 ± 1.5 | 50.1 ± 3.6 |
| 22 | thiophene-CH | 4-O-phenyl-CH | 94.6 ± 0.0 | 87.5 ± 2.6 |
| 23 | methylfuran-CH | phenyl-CH | 24.7 ± 10.4 | 32.6 ± 3.0 |
| 24 | 4-OEt-phenyl | 4-O-phenyl-CH | 96.7 ± 0.6 | 88.0 ± 0.7 |
| 25 | furan-CH | 4-F-phenyl-CH | 62.1 ± 1.4 | 53.8 ± 0.2 |
| 26 | 2-OMe-phenyl-CH | 4-O-phenyl-CH | 91.2 ± 0.8 | 80.6 ± 0.4 |

| Second generation analogs | | | | |
|---|---|---|---|---|
| 27 |  |  | 96.2 ± 0.3 | 92.1 ± 0.4 |
| 28 |  |  | 96.5 ± 0.1 | 93.8 ± 0.4 |
| 29 |  |  | 92.3 ± 0.2 | 77.8 ± 1.2 |
| 30 |  |  | 100.0 ± 0.0 | 100.0 ± 0.0 |
| 31 |  |  | 94.6 ± 0.7 | 79.3 ± 0.3 |

INHIBITORS OF UDP-GALACTOPYRANOSE MUTASE

CROSS-REFERENCES TO RELATED APPLICATIONS

This application is a divisional of U.S. patent application Ser. No. 14/728,914, filed Jun. 2, 2015, which claims the benefit of U.S. provisional application 62/007,355, filed Jun. 3, 2014. Each of these applications is incorporated by reference herein in its entirety.

STATEMENT REGARDING GOVERNMENT SUPPORT

This invention was made with government support under AI063596 and GM059957 awarded by the National Institutes of Health. The government has certain rights in the invention.

BACKGROUND OF THE INVENTION

Carbohydrates are the most ubiquitous class of biomolecules in nature, yet glycan diversity imparts unique sugar features that can be targeted in a species-specific manner. The monosaccharide galactofuranose (Galf) is found in cell surface glycoconjugates of many human pathogens. However, Galf is absent from the mammalian glycome [Richards, M. R. and T. L. Lowary, Chemistry and Biology of Galactofuranose-Containing Polysaccharides. Chem Bio Chem, 2009. 10(12): p. 1920-1938], making enzymes involved in metabolism of the sugar attractive targets for treatment of human disease.

Galf contributes to virulence in infectious microbes such as *Klebsiella pneumoniae* (Kp) [Richards et al. 2009], *Leishmania major*, and *Aspergillus fumigatus* [Tefsen, B., et al., Galactofuranose in eukaryotes: aspects of biosynthesis and functional impact. Glycobiology, 2012. 22(4):456-469], as well as certain multicellular eukaryotic pathogens [Wesener, D. A., et al., UDP-galactopyranose mutase in nematodes. Biochemistry, 2013. 52(25):4391-8]. *Mycobacterium tuberculosis*, the causative agent of tuberculosis, harbors an essential Galf polysaccharide known as galactan within its renown thick and hydrophobic cell wall complex [Pan, F., et al., *Cell Wall Core Galactofuran Synthesis Is Essential for Growth of Mycobacteria*. J Bacteriol, 2001. 183(13):3991-3998]. Tuberculosis causes an estimated 2 million deaths worldwide every year (WHO report 2014). With the rise of multidrug-resistant and extremely drug resistant *M. tuberculosis* (Mt), tuberculosis is becoming increasingly difficult to treat (WHO report 2014). This underscores the need for new drug candidates in the pipeline.

Cell wall biosynthetic enzymes are targets of several first-line antitubercular drugs, including isoniazid and ethambutol [Richards et al. 2009; Pan et al. 2001]. Uridine 5'-diphosphate (UDP)-galactopyranose mutase (UGM) generates the biological source of UDP-Galf, utilized by galactofuranosyl transferases for construction of the mycobacterial cell wall galactan. UGM is a flavin-dependent protein that catalyzes ring contraction of UDP-galactopyranose (UDP-Galp) to form UDP-Galf [Soltero-Higgin, M., et al., A unique catalytic mechanism for UDP-galactopyranose mutase. Nat Struct Mol Biol, 2004. 11(6): 539-543] (FIG. 1), the five-membered ring isomer of nucleotide-linked galactose. UGM has been validated as a mycobacterial drug target [Dykhuizen, E. C., et al., Inhibitors of UDP-galactopyranose mutase thwart mycobacterial growth. J Am Chem Soc, 2008. 130(21):6706-7; Borrelli, S., et al., Antimycobacterial activity of UDP-galactopyranose mutase inhibitors. Int. J Antimicrob Agents, 2010. 36(4):364-8], and thus small molecule UGM antagonists are highly sought after.

Most efforts to develop UGM inhibitors have focused on UDP-sugar substrate analogs. (Caravano, A.; Dohi, H.; Sinay, P.; Vincent, S. P. Chem.-Eur. J. 2006, 12, 3114-3123; Liautard, V.; Christina, A. E.; Desvergnes, V.; Martin, O. R. J. Org. Chem. 2006, 71, 7337-7345; Ghavami, A.; Chen, J. J. W.; Pinto, B. M. Carbohydr. Res. 2004, 339, 401-407; Lee, R. E.; Smith, M. D.; Pickering, L.; Fleet, G. W. J. Tetrahedron Lett. 1999, 40:8689-8692; Liautard, V.; Desvergnes, V.; Martin, O. R. Org. Lett. 2006, 8, 1299-1302.) Simple sugar derivatives, including galactopyranose or galactofuranose analogs, bind weakly with affinities in the millimolar range (Lee, R. E.; Smith, M. D.; Nash, R. J.; Griffiths, R. C.; McNeil, M.; Grewal, R. K.; Yan, W. X.; Besra, G. S.; Brennan, P. J.; Fleet, G. W. J. Tetrahedron Lett. 1997, 38, 6733-6736; Veerapen, N.; Yuan, Y.; Sanders, D. A. R.; Pinto, B. M. Carbohydr. Res. 2004, 339, 2205-2217.) Inhibitors that incorporate the uridine portion of the substrate bind substantially better, with affinities that approximate that of UDP-Galp (Kd=52 µM) (Itoh, K.; Huang, Z. S.; Liu, H. W. Org. Lett. 2007, 9, 879-882; Caravano, A.; Vincent, S. P.; Sinay, P. Chem. Commun. 2004, 1216-1217; Caravano, A.; Mengin-Lecreulx, D.; Brondello, J. M.; Vincent, S. P.; Sinay, P. Chem.-Eur. J. 2003, 9, 5888-5898; Pan, W. D.; Ansiaux, C.; Vincent, S. P. Tetrahedron Lett. 2007, 48, 4353-4356; Scherman, M. S.; Winans, K. A.; Stern, R. J.; Jones, V.; Bertozzi, C. R.; McNeil, M. R. Antimicrob. Agents Chemother. 2003, 47, 378-382.) These approaches have not yet afforded compounds that block mycobacterial growth.

Certain non-substrate based molecules have been identified as UMG ligands. For example, certain nitrofuranylamides have been identified as inhibitors of UGM catalysis and mycobacterial growth. (Tangallapally, R. P.; Yendapally, R.; Lee, R. E.; Hevener, K.; Jones, V. C.; Lenaerts, A. J. M.; McNeil, M. R.; Wang, Y. H.; Franzblau, S.; Lee, R. E. J. Med. Chem. 2004, 47, 5276-5283.) Nevertheless, the UGM inhibition and antimycobacterial activity of these compounds were not correlated, so they do not address the utility of inhibiting UGM.

Published International application WO 2005/007625 (Lee et al.), as well as published U.S. application 20050222408, relate to certain heterocyclic amides with anti-tuberculosis activity. More specifically, these patent documents relate to compounds of formula:

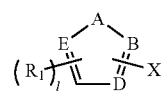

wherein A is selected from the group consisting of oxygen, sulfur, and $NR_{15}$, where $R_{15}$ is selected from the group consisting of H, alkyl, aryl, substituted alkyl, and substituted aryl; B, D, and E are each independently selected from the group consisting of CH, nitrogen, sulfur and oxygen; $R_1$ is selected from the group consisting of nitro, halo, alkyl ester, arylsulfanyl, arylsulfinyl, arylsulfonyl and sulfonic acid; t is an integer from 1 to 3; and X is a substituted amide. These patent documents are incorporated by reference herein at least in part for the definitions of structural elements of the above formula.

A fluorescence polarization (FP) based assay has been developed that allows detection of competitive UGM inhibitors [Soltero-Higgin, M., et al., Identification of inhibitors for UDP-galactopyranose mutase. J Am Chem Soc, 2004. 126(34): p. 10532-3; Dykhuizen, E. C. and L. L. Kiessling, Potent ligands for prokaryotic UDP-galactopyranose mutase that exploit an enzyme subsite. Org Lett, 2009. 11(1): p. 193-6]. Using this FP assay, several high-throughput screens (HTS) have been conducted, endeavoring discovery of small molecule UGM ligands [Soltero-Higgin et al. 2004; Carlson, E. E., J. F. May, and L. L. Kiessling, Chemical probes of UDP-galactopyranose mutase. Chem Biol, 2006. 13(8): p. 825-37]. The screens culminated in fairly low hit rates, revealing the challenging nature of UGM as a target. Nonetheless, through HTS, one series of thiazolidinones (TZ) with considerable activity towards UGM was discovered [Soltero-Higgin et al. 2004]. The TZ series was optimized through scaffold hopping to a 2-aminothiazole (AT) inhibitor core [Dykhuizen, et al., 2008]. The most potent AT displays an $IC_{50}$ of 7.2 µM and 37 µM against KpUGM and MtUGM, respectively [Dykhuizen, et al. 2008; Borrelli et al. 2010].

U.S. Pat. No. 8,273,778 issued Sep. 25, 2012 relates to inhibitors of UDP-galactopyranose mutase having among others, 2-aminothiazole structures. This issued patent is incorporated by reference herein in its entirety for descriptions of the UDP-galactopyranose mutase inhibitors there as well as methods of assessing such inhibitors and methods of application of such inhibitors.

While a number of small molecule inhibitors of UDP-galactopyranose mutase have been identified, there remains a need in the art for additional inhibitors which exhibit effective inhibition of microorganisms having UDP-galactopyranose mutase.

SUMMARY OF THE INVENTION

The invention provides compounds which inhibit microbial growth or attenuate the virulence of pathogenic microorganisms. In certain embodiments, compounds of the invention inhibit UDP-galactopyranose mutase (UGM) and have activity as inhibitors of microbial growth of microorganisms which contain this enzyme and particularly those microorganisms in which this enzyme is responsible for the incorporation of galactofuranose residues, particularly for uridine 5'-diphosphate (UDP) galactopyranose mutase. In certain embodiments, compounds of the invention inhibit UDP-galactopyranose mutase (UGM) and have activity to attenuate virulence of pathogenic microorganisms which contain this enzyme and particularly those microorganisms in which this enzyme is responsible for the incorporation of galactofuranose residues.

More specifically, the inhibitors of UGM of this invention inhibit growth or attenuate virulence of microbial pathogens including *mycobacterium*, for example, *M. tuberculosis* and *M. smegmatis* and *Klebsiella*, for example, *Klebsiella pneumoniae*. Additionally, UGM inhibitors of this invention can also inhibit UGM of certain eukaryotic human and animal pathogens, those of fungi and nematodes in particular. Compounds of this invention are useful for treatment of infections by prokaryotic and eukaryotic pathogens. Compounds of this invention are useful in human and veterinary treatment applications. Compounds of this invention are useful for the treatment of tuberculosis. Compounds of this invention are useful in combination therapy with other antibiotics for the treatment of microbial infections, including tuberculosis. Compounds of this invention are useful for the treatment of multiple drug resistant microbial infections, including multiple drug resistant tuberculosis.

Compounds of the invention include triazolothiadiazines, particularly 3,6,7-substituted-7H-[1,2,4]triazolo[3,4-b][1,3,4]thiadiazines, and 4-(1H-pyrrol-3-yl) thiazoles, particularly 4-(1,2,5-substituted-1H-pyrrol-3-yl)-2-substituted thiazoles.

The invention provides triazolthidiazine compounds of formula I:

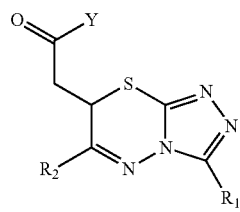

and salts thereof,
where:

Y is —$OR_3$, is or —$NH_2$, $R_3$ is hydrogen, or an optionally substituted alkyl, cycloalkyl, alkenyl, cycloalkenyl, heterocyclyl, aryl or heteroaryl group, and $R_1$ and $R_2$ are independently optionally substituted aryl or heteroaryl groups having one or two rings or are alkyl groups substituted with an optionally substituted aryl, aryloxy, heteroaryl or heteroaryloxy group having one or two rings, particularly those having two fused rings; and where optional substitution is substitution with one or more halogen, nitro, cyano, isocyano, thiocyano, isothiocyano, hydroxyl, $C_1$-$C_6$ alkyl, $C_1$-$C_6$ alkoxy, sulfonamide (—$SO_2$—$N(R_F)_2$), azide, sulfonyl (—$SO_2$—$R_F$), —$COOR_F$, —$COR_F$, —$CON(R_F)_2$, —$N(R_F)_2$, and $C_1$-$C_6$ haloalkyl groups, including among others trifluoromethyl, trichloromethyl and tribromomethyl groups, where $R_F$ is hydrogen or a $C_1$-$C_6$ alkyl group. Compounds of formula I are useful for inhibition of mycobacteria or other microorganisms and/or as intermediates in the synthesis of inhibition of mycobacteria.

In specific embodiments, Y is —$OR_3$. In specific embodiments, $R_3$ is hydrogen. In specific embodiments, $R_3$ is an unsubstituted alkyl group having 1-3 carbon atoms. In specific embodiments, $R_3$ is an unsubstituted cycloalkyl group having 3-8 carbon atoms. Alkyl and cycloalkyl groups of $R_3$ can, in an embodiment, be optionally substituted with one or more halogens. In specific embodiments, $R_3$ is an unsubstituted alkyl group having 6-12 carbon atoms. In other specific embodiments, the $R_1$ and $R_2$ groups both contain optionally substituted aryl or aryloxy groups, preferably optionally substituted phenyl or phenoxy (Ph-O—) groups. In specific embodiments, optional substitution is substitution with one or more halogens, nitro, cyano, azide or haloalkyl groups. In specific embodiments, $R_1$ and $R_2$ are substituted phenyl groups or substituted benzyl groups. In specific embodiments, $R_1$ and $R_2$ are substituted phenoxy groups or substituted benzyloxy groups. In specific embodiments, one of $R_1$ or $R_2$ is a para-iodo phenyl group or a para-iodobenzyl group.

The invention also provides 4-(1H-pyrrol-3-yl)thiazole compounds of formula II:

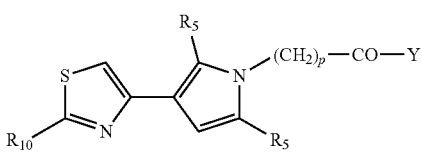

and pharmaceutically acceptable salts thereof,
where:
Y is —$OR_4$, or —$NH_2$;
p is 1, 2 or 3;
$R_4$ is hydrogen, or an optionally substituted alkyl, cycloalkyl, alkenyl, cycloalkenyl, heterocyclyl, aryl or heteroaryl group;
each $R_5$ is independently hydrogen or an optionally substituted alkyl group having 1-3 carbon atoms;
$R_{10}$ is hydrogen or an —$NR_6R_7$ group, where:
  $R_6$ is hydrogen, or optionally substituted alkyl, cycloalkyl, alkenyl, cycloalkenyl, heterocyclyl, aryl or heteroaryl groups; and
  $R_7$ is hydrogen, or optionally substituted alkyl, cycloalkyl, alkenyl, cycloalkenyl, heterocyclyl, aryl or heteroaryl groups:
where optional substitution is substitution with one or more halogen, nitro, cyano, isocyano, thiocyano, isothiocyano, hydroxyl, $C_1$-$C_6$ alkyl, $C_1$-$C_6$ alkoxy, sulfonamide (—$SO_2$—$N(R_F)_2$), azide, sulfonyl (—$SO_2$—$R_F$), —$COOR_F$, —$COR_F$, —$CON(R_F)_2$, —$N(R_F)_2$, and $C_1$-$C_6$ haloalkyl groups, including trifluoromethyl, trichloromethyl and tribromomethyl groups, where $R_F$ is hydrogen or a $C_1$-$C_6$ alkyl group. Compounds of formula II are useful for inhibition of mycobacteria or other microorganisms and/or as intermediates in the synthesis of inhibition of mycobacteria.

In specific embodiments of formula II, Y is —$OR_4$. In specific embodiments, $R_4$ is hydrogen. In specific embodiments, $R_4$ is an alkyl group having 1-3 carbon atoms. In specific embodiments, $R_4$ is an cycloalkyl group having 3-8 carbon atoms. In specific embodiments, $R_4$ is an alkyl group having 6-12 carbon atoms. In specific embodiments, both $R_5$ are methyl groups or one $R_5$ is hydrogen and the other is methyl In other specific embodiments, one $R_6$ is hydrogen or a $C_1$-$C_3$ alkyl group and the $R_7$ group is a substituted aryl group or an alkyl group substituted with a substituted aryl group, preferably a substituted phenyl groups. In specific embodiments, optional substitution is substitution with one or more halogens, nitro, cyano, azide or haloalkyl groups. In specific embodiments, $R_7$ is a substituted benzyl group. In specific embodiments, $R_7$ is a 1-arylethy group, where the aryl group is substituted. In specific embodiments, $R_7$ is a 1-phenylethyl group, where the phenyl group is substituted. In specific embodiments, $R_7$ contains a halo-substituted phenyl group. In specific embodiments, $R_7$ contains a p-iodophenyl group.

In specific embodiments, compounds of the invention exhibit low cytotoxicity with LD50 of 200 µM or less for human or animal cells. In more specific embodiments, compounds of the invention exhibit cytotoxity of LD50 of 100 or less for human or animal cells. Preferred compounds of the invention for treatment of a human or animal for a given microorganism (bacterial, fungus, algae or nematode) exhibit LD50 for cells of the human or animal which is at least 4-fold more preferably 5-fold lower than the MIC of the compound for a given microorganism.

The invention provides pharmaceutically acceptable compositions which comprise one or more compounds of formula I or II and a pharmaceutically acceptable excipient. In specific embodiments, the excipient is other than water. In specific embodiments, the excipient is other than a solvent.

The invention provides methods for inhibiting UGM comprising contacting UGM with an amount of one or more of the compounds of formulas I or II which is effective for inhibiting the enzyme.

The invention provides a method for inhibiting incorporation of Galf into a microbial polysaccharide which comprises contacting the microorganism or an environment containing the organism with an amount one or more compounds of formulas I or II effective for such inhibition.

The invention also provides methods for inhibiting the growth of mycobacteria which comprises contacting the mycobacteria or an environment containing the mycobacteria with an amount of one or more compounds of formulas I or II effective for such growth inhibition.

The invention also provides methods for treatment of a mycobacterial infection which comprises administering to a human or non-human subject in need of such treatment an amount of one or more compounds of formula I or II effective for such treatment. In a specific embodiment, the mycobacterial infection is tuberculosis.

BRIEF DESCRIPTION OF THE DRAWINGS

(FIG. 2A) property matched decoys or (FIG. 2B) the entire 4.7 million lead-like ZINC library. The area under the curve for ligands from the AT scaffold or both AT+TZ scaffolds is indicated. The dashed line corresponds to the performance of a random ranking of the library.

FIG. 3A shows the structures (identified by number) of select molecules from the top-ranking 0.01% of the docking library, which were tested for inhibition of KpUGM in vitro. Docking rank from the virtual screen is indicated in parentheses.

FIGS. 4A and 4B are graphs showing probe displacement in a competitive-binding FP assay, for compound (22) and compound (30) with Kd values of 9.2 and 4.7 µM, respectively. Lineweaver-Burk analysis confirmed that 22 and 30 are competitive UGM inhibitors (FIGS. 4C and 4D, respectively). Both compounds display a Ki in the low micromolar range (Ki, 22=7.0 µM and Ki, 30=1.1 µM), with 30 being about 5-fold more potent than 22 in vitro. The complementary nonlinear regression plot of KpUGM inhibition by 30 is shown (FIG. 4E) for comparison to double reciprocal analysis. FIG. 4F (left) is a graph of the alamar blue assay used to assess M. smegmatis viability in liquid culture. FIG. 4F (right) shows MICs were determined after 46 hours of growth in the presence of select UGM inhibitors. While 22 showed no M. smegmatis growth repression at the tested concentrations, 30 showed potent antimycobacterial activity, with a MIC of 20 µM.

FIG. 11B is a graph assessing KpUGM inhibition in vitro where compound 14 showed increased dose-dependent KpUGM inhibition in vitro. FIG. 11C is a graph assessing Kd, where compound 14 also proved a slightly tighter binder (Kd=4.5 µM) (right) than the lead compound.

DETAILED DESCRIPTION OF THE INVENTION

Figure 1:
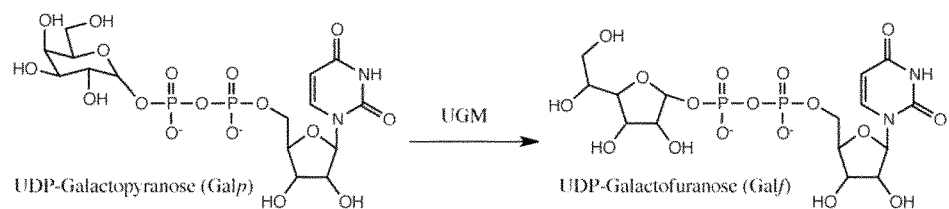
FIG. 1 is a scheme of the isomerization reaction catalyzed by UGM.

This invention is at least in part based on structure-based virtual screening for inhibitors of UDP-galactopyranose mutase. More specifically, small molecule UGM ligands were predicted in silico, and top-ranking molecules were tested for activity in enzyme assays. In this way, a series of competitive UGM inhibitors that not only inhibit UGM in vitro but also possess antimycobacterial activity have been identified.

In silico structure-based virtual screening [Shoichet, B. K., Virtual screening of chemical libraries. Nature, 2004. 432(7019): p. 862-5] is a computational approach complementary to empirical HTS for identification of small molecule binders of a specific protein target [Ferreira, R. S., et al., Complementarity between a docking and a high-throughput screen in discovering new cruzain inhibitors. J Med Chem, 2010. 53(13): p. 4891-905]. Virtual screening has been shown to have better hit-rates than HTS as well as aid in discovery of more chemically novel leads [Babaoglu, K., et al., Comprehensive mechanistic analysis of hits from high-throughput and docking screens against beta-lactamase. J Med Chem, 2008. 51(8): p. 2502-11]. This method is highly cost effective and allows screening of a broad scope of small molecules, many of which are not part of established HTS screening decks. Virtual screening hits are often weaker binders compared to HTS. However, this can be advantageous, as HTS is at times overly stringent, and thus may overlook weaker binding ligands that could yield potent, specific inhibitors after lead optimization and structure-activity relationship (SAR) analyses.

In the present work, the DOCK program [Lorber, D. M. and B. K. Shoichet, Hierarchical docking of databases of multiple ligand conformations. Curr Top Med Chem, 2005. 5(8): p. 739-49; Mysinger, M. M. and B. K. Shoichet, Rapid context-dependent ligand desolvation in molecular docking. J Chem Inf Model, 2010. 50(9): p. 1561-73] was used to virtually screen a database of 4.7 million commercially available compounds for competitive UGM ligands. Through exploring the SAR of a weak binding hit from the screen, potent UGM inhibitors with marked antimycobacterial activity were identified.

The compounds identified contain either a bicyclic triazolo thiadiazine core with diversified aromatic substituents (Formula I) or a 1H-pyrrol-3-ylthiazole structure with various substituents (Formula II).

Additionally, the structure of the first UGM-small molecule complex has been identified. This structure can guide further optimization of this inhibitor series.

The inhibitors of this invention are useful for inhibition of growth of microorganisms, including bacteria and eukaryotic organisms, such as protozoa and nematodes and the treatment of diseases caused by such organisms. In a specific embodiment, the inhibitors of this invention are useful for inhibition of growth of mycobacteria, and for the treatment of mycobacterial disease. Further the inhibitors of this invention are useful as tools to probe the role of UGM in biological systems. The invention also provided compounds which can be employed as intermediates in the synthesis of additional UGM inhibitors having the structures of formula I and II.

In specific embodiments of formula I, $R_1$ is selected from hydrogen, fur-2-yl, p-F-phenyl, p-F-benzyl, thien-2-yl, 1-methylfur-3-yl, p-Cl-phenoxy-$CH_2$—, o-methoxyphenyl, p-F-phenyl, p-F-benzyl, p-Br-benzyl, p-Br-phenyl, p-Cl-phenyl, p-Cl-benzyl.

In specific embodiments of formula I, $R_2$ is selected from p-F-phenyl, p-F-benzyl, p-F-phenyl, p-Cl-benzyl p-Cl-phenyl, p-Br-benzyl, p-Br-phenyl, thien-2-yl, phenyl, or p-methylphenyl.

In specific embodiments of formula I, $R_1$ is selected from hydrogen, fur-2-yl, p-F-phenyl, p-F-benzyl, thien-2-yl, 1-methylfur-3-yl, p-Cl-phenoxy-$CH_2$—, o-methoxyphenyl, p-F-phenyl, p-F-benzyl, p-Br-benzyl, p-Br-phenyl, p-Cl-phenyl, p-Cl-benzyl and $R_2$ is selected from p-F-phenyl, p-F-benzyl, p-F-phenyl, p-Cl-benzyl p-Cl-phenyl, p-Br-benzyl, p-Br-phenyl, thien-2-yl, phenyl, or p-methylphenyl.

In specific embodiments of formula I, $R_1$ is selected from hydrogen, fur-2-yl, p-F-phenyl, p-F-benzyl, thien-2-yl, 1-methylfur-3-yl, p-Cl-phenoxy-$CH_2$—, o-methoxyphenyl, p-F-phenyl, p-F-benzyl, p-Br-benzyl, p-Br-phenyl, p-Cl-phenyl, p-Cl-benzyl and $R_2$ is selected from p-F-phenyl, p-F-benzyl, p-F-phenyl, p-Cl-benzyl p-Cl-phenyl, p-Br-benzyl, p-Br-phenyl, thien-2-yl, phenyl, or p-methylphenyl with the exception that the compound is a compound other than compound 6 or a compound other than compounds 16-31.

In specific embodiments of formula I, $R_1$ is p-I-phenyl.
In specific embodiments of formula I, $R_1$ is p-I-benzyl.
In specific embodiments of formula I, $R_2$ is selected from p-F-phenyl, p-F-benzyl, p-F-phenyl, p-Cl-benzyl p-Cl-phenyl, p-Br-benzyl, p-Br-phenyl, thien-2-yl, phenyl, or p-methylphenyl.

In specific embodiments of formula I, $R_1$ is p-Br-phenyl-; p-Cl-phenyl; p-Cl-benzyl; p-I-phenyl; p-I-benzyl; p-Br-phenoxy-$CH_2$—; p-I-phenoxy-$CH_2$—; or p-F-phenoxy-$CH_2$—.

In specific embodiments of formula I, $R_2$ is p-halo-benzyl.
In specific embodiments of formula I, $R_2$ is p-Br-benzyl.
In specific embodiments of formula I, $R_2$ is p-I-benzyl.
In specific embodiments of formula I, $R_2$ is p-I-phenyl.
In specific embodiments of formula I:
$R_2$ is 2-thienyl and $R_1$ is p-Br-benzyl, p-Cl-benzyl, p-I-benzyl, p-halophenyl, p-methylphenyl or phenyl;
$R_2$ is p-Cl-phenyl and $R_1$ is p-F-benzyl, p-Cl-phenyl, p-Cl-benzyl, p-Cl-phenoxy-$CH_2$—, p-Br-phenyl, p-I-phenyl or p-I-benzyl;
$R_2$ is p-methylphenyl and $R_1$ is p-Br-phenyl, p-Br-benzyl, p-Cl-phenyl, p-Cl-benzyl, p-I-phenyl, or p-I-benzyl;
$R_2$ is phenyl and $R_1$ is p-Br-phenyl, p-Br-benzyl, p-Cl-phenyl, p-Cl-benzyl, p-I-phenyl or p-I-benzyl;
$R_2$ is p-F-phenyl and $R_1$ is p-F-phenyl, p-F-benzyl, p-Cl-phenoxy-$CH_2$—, or thien-2-yl;
$R_2$ is o-methoxyphenyl and $R_1$ is p-F-phenyl, p-F-benzyl, p-Cl-phenoxy-$CH_2$, thien-2-yl, p-Br-phenyl, p-Br-benzyl, p-I-phenyl, p-I-benzyl or p-C-benzyl.
$R_1$ is p-F-phenyl and $R_2$ is p-F-phenyl, p-F-benzyl, p-Cl-benzyl, thien-2-yl, p-I-phenyl, p-I-benzyl, p-Br-phenyl, or p-Br-benzyl;
$R_1$ is p-F-benzyl and $R_2$ is p-Cl-phenyl, p-Cl-benzyl, p-I-phenyl, p-I-benzyl, p-Br-phenyl, or p-Br-benzyl;
$R_1$ is p-Br-benzyl and $R_2$ is thien-2-yl, p-Cl-benzyl, p-Br-phenyl, p-Br-benzyl, p-I-phenyl, or p-I-benzyl;
$R_1$ is fur-2-yl and $R_2$ is p-Br-phenyl;
$R_1$ is thien-2-yl and $R_2$ is p-F-phenyl, p-Br-phenyl, or p-I-phenyl; or
$R_1$ is p-Cl-phenoxy-$CH_2$— and $R_2$ is p-F-phenyl, p-F-benzyl, p-Cl-phenyl, p-Cl-benzyl, p-Br-phenyl, p-Br-benzyl, p-I-phenyl, or p-I-benzyl.

In specific embodiments, one of $R_1$ or $R_2$ is a dichloro-, difluoro- or dibromophenyl.

In specific embodiments, one of $R_1$ or $R_2$ is a o, p-dichloro-, o, p-difluoro- or o, p-dibromophenyl.

In specific embodiments, one of $R_1$ or $R_2$ is a m, m-dichloro-, m, m-difluoro- or m, m-dibromophenyl.

In specific embodiments, the invention provides compounds of formula IA:

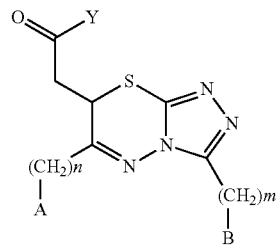

and salts thereof
where:
Y is as defined for formula I and preferably Y is —$OR_3$ and more preferably $R_3$ is hydrogen;
n and m are 0 or 1, including both n and m=0, n=0 and m=1 or n=1 and m=0;
A and B are optionally substituted phenyl rings or are heteroaromatic rings, including thien-2-yl, fur-2-yl and fur-3-yl.

In specific embodiments, A and B are both optionally substituted phenyl rings. In specific embodiments at least one of A and B is substituted. In specific embodiments, at least one of A and B is substituted with one or more halogens. In specific embodiments, at least one of A and B is substituted with two or three halogens. In specific embodiments, one of A or B is a heteroaryl group.

In specific embodiments, the invention provides compounds of formula IB:

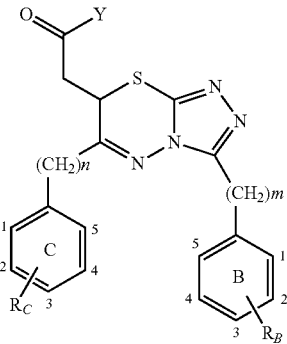

and salts thereof
where:
Y is as defined for formula I and preferably Y is —$OR_3$ and more preferably $R_3$ is hydrogen;
n and m are 0 or 1, including both n and m=0, n=0 and m=1 or n=1 and m=0;
$R_C$ and $R_B$ represent optional substitution on the indicated phenyl rings, where preferred optional substitution is as defined as formula I above. In specific embodiments, optional substitution is substitution with one to five halogens, one or two nitro, cyano, isocyano, or thiocyano groups or one to three $C_1$-$C_3$ alkoxy group (particularly methoxy groups), or one or two $C_1$-$C_3$ alkyl groups (particularly methyl groups).

In specific embodiments of formula IB:
$R_B$ is substitution by five halogens on the B ring;
$R_B$ is substitution by five fluorines on the B ring;
$R_B$ is substitution by three halogens on the B ring;

$R_B$ is substitution by three chlorines on the B ring;
$R_B$ is substitution by three bromines on the B ring;
$R_B$ is substitution by three fluorines on the B ring;
$R_B$ is substitution by three iodines on the B ring;
$R_B$ is substitution by halogens at carbons 2, 3 and 4 on the B ring (see formula IB);
$R_B$ is substitution by chlorines at carbons 2, 3 and 4 on the B ring;
$R_B$ is substitution by fluorines at carbons 2, 3 and 4 on the B ring;
$R_B$ is substitution by bromines at carbons 2, 3 and 4 on the B ring;
$R_B$ is substitution by iodines at carbons 2, 3 and 4 on the B ring;
$R_B$ is substitution by halogens at carbons 1, 2 and 3 on the B ring;
$R_B$ is substitution by chlorines at carbons 2, 3 and 4 on the B ring;
$R_B$ is substitution by two halogens on the B ring;
$R_B$ is substitution by two chlorines on the B ring;
$R_B$ is substitution by two bromines on the B ring;
$R_B$ is substitution by two iodines on the B ring;
$R_B$ is substitution by two fluorines on the B ring;
$R_B$ is substitution by halogens at carbons 2 and 4 on the B ring;
$R_B$ is substitution by fluorines at carbons 2 and 4 on the B ring;
$R_B$ is substitution by chlorines at carbons 2 and 4 on the B ring;
$R_B$ is substitution by bromines at carbons 2 and 4 on the B ring;
$R_B$ is substitution by iodines at carbons 2 and 4 on the B ring;
$R_B$ is substitution by halogens at carbons 1 and 3 on the B ring;
$R_B$ is substitution by fluorines at carbons 1 and 3 on the B ring;
$R_B$ is substitution by chlorines at carbons 1 and 3 on the B ring;
$R_B$ is substitution by bromines at carbons 1 and 3 on the B ring;
$R_B$ is substitution by iodines at carbons 1 and 3 on the B ring;
$R_B$ is substitution by halogens at carbons 2 and 3 on the B ring;
$R_B$ is substitution by fluorines at carbons 2 and 3 on the B ring;
$R_B$ is substitution by chlorines at carbons 2 and 3 on the B ring;
$R_B$ is substitution by bromines at carbons 2 and 3 on the B ring;
$R_B$ is substitution by iodines at carbons 2 and 3 on the B ring;
$R_B$ is substitution by one halogen on the B ring;
$R_B$ is substitution by one fluorine on the B ring;
$R_B$ is substitution by one chlorine on the B ring;
$R_B$ is substitution by one bromine on the B ring;
$R_B$ is substitution by one iodine on the B ring;
$R_B$ is substitution by one halogen on carbon 3 of the B ring;
$R_B$ is substitution by one fluorine on carbon 3 of the B ring;
$R_B$ is substitution by one chlorine on carbon 3 of the B ring;
$R_B$ is substitution by one chlorine on carbon 2 of the B ring;
$R_B$ is substitution by one chlorine on carbon 1 of the B ring;
$R_B$ is substitution by one bromine on carbon 3 of the B ring;
$R_B$ is substitution by one iodine on carbon 3 of the B ring;
$R_B$ is substitution by one nitro group on the B ring;
$R_B$ is substitution by one nitro group on carbon 2 of the B ring;
$R_B$ is substitution by one nitro group on carbon 3 of the B ring;
$R_B$ is substitution by one hydroxyl group on the B ring;
$R_B$ is substitution by one hydroxyl group on carbon 3 of the B ring;
$R_B$ is substitution by one methoxy group on the B ring;
$R_B$ is substitution by one methoxy group on carbon 3 of the B ring;
$R_B$ is substitution by one cyano group on the B ring;
$R_B$ is substitution by one cyano group on carbon 3 of the B ring;
$R_B$ is substitution by a C1-C6 alkyl group at carbon 3 of the B ring;
$R_B$ is substitution by a nitro group at carbon 2 and a halogen at carbon 3 of the B ring;
$R_B$ is substitution by a nitro group at carbon 2 and a chlorine at carbon 3 of the B ring;
$R_B$ is substitution by a C1-C3 alkyl group at carbon 1 and a halogen at carbon 3 of the B ring;
$R_B$ is substitution by a C1-C3 alkyl group at carbon 1 and a hydroxy at carbon 3 of the B ring; or
$R_B$ is substitution including two different substituents on the B ring.

The various embodiments of B ring substitution above can be combined with the various embodiments of C ring substitution below.

In specific embodiments of formula IB:
$R_C$ is substitution by five halogens on the C ring;
$R_C$ is substitution by five fluorines on the C ring;
$R_C$ is substitution by three halogens on the C ring;
$R_C$ is substitution by three chlorines on the C ring;
$R_C$ is substitution by three bromines on the C ring;
$R_C$ is substitution by three fluorines on the C ring;
$R_C$ is substitution by three iodines on the C ring;
$R_C$ is substitution by halogens at carbons 2, 3 and 4 on the C ring;
$R_C$ is substitution by chlorines at carbons 2, 3 and 4 on the C ring;
$R_C$ is substitution by fluorines at carbons 2, 3 and 4 on the C ring;
$R_C$ is substitution by bromines at carbons 2, 3 and 4 on the C ring;
$R_C$ is substitution by iodines at carbons 2, 3 and 4 on the C ring;
$R_C$ is substitution by two halogens on the C ring;
$R_C$ is substitution by two chlorines on the C ring;
$R_C$ is substitution by two bromines on the C ring;
$R_C$ is substitution by two iodines on the C ring;
$R_C$ is substitution by two fluorines on the C ring;
$R_C$ is substitution by halogens at carbons 2 and 4 on the C ring;
$R_C$ is substitution by fluorines at carbons 2 and 4 on the C ring;
$R_C$ is substitution by chlorines at carbons 2 and 4 on the C ring;
$R_C$ is substitution by bromines at carbons 2 and 4 on the C ring;
$R_C$ is substitution by iodines at carbons 2 and 4 on the C ring;
$R_C$ is substitution by halogens at carbons 1 and 3 on the C ring;
$R_C$ is substitution by fluorines at carbons 1 and 3 on the C ring;
$R_C$ is substitution by chlorines at carbons 1 and 3 on the C ring;
$R_C$ is substitution by bromines at carbons 1 and 3 on the C ring;
$R_C$ is substitution by iodines at carbons 1 and 3 on the C ring;

$R_C$ is substitution by halogens at carbons 2 and 3 on the C ring;
$R_C$ is substitution by fluorines at carbons 2 and 3 on the C ring;
$R_C$ is substitution by chlorines at carbons 2 and 3 on the C ring;
$R_C$ is substitution by bromines at carbons 2 and 3 on the C ring;
$R_C$ is substitution by iodines at carbons 2 and 3 on the C ring;
$R_C$ is substitution by one halogen on the C ring;
$R_C$ is substitution by one fluorine on the C ring;
$R_C$ is substitution by one chlorine on the C ring;
$R_C$ is substitution by one bromine on the C ring;
$R_C$ is substitution by one iodine on the C ring;
$R_C$ is substitution by one halogen on carbon 3 of the C ring;
$R_C$ is substitution by one fluorine on carbon 3 of the C ring;
$R_C$ is substitution by one chlorine on carbon 3 of the C ring;
$R_C$ is substitution by one bromine on carbon 3 of the C ring;
$R_C$ is substitution by one iodine on carbon 3 of the C ring;
$R_C$ is substitution by one nitro group on the C ring;
$R_C$ is substitution by one nitro group on carbon 2 of the C ring;
$R_C$ is substitution by one nitro group on carbon 3 of the C ring;
$R_C$ is substitution by one hydroxyl group on the C ring;
$R_C$ is substitution by one hydroxyl group on carbon 3 of the C ring;
$R_C$ is substitution by one cyano group on the C ring; or
$R_C$ is substitution by one cyano group on carbon 3 of the C ring;

In specific embodiments, the invention provides compounds of formula IIA:

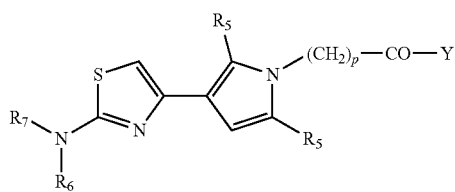

and salts thereof
where: Y, p, $R_5$ $R_7$ and $R_8$ are as defined above.

In specific embodiments, the invention provides compounds of formula II other than compounds 10, 14 and 15.
In specific embodiments, $R_6$ is hydrogen or methyl. In specific embodiments, $R_7$ is an optionally substituted phenyl, an optionally substituted benzyl or a 1-phenylethyl group, where the phenyl group is optionally substituted. In specific embodiments, $R_7$ contains a substituted phenyl group. In specific embodiments, $R_7$ contains a p-halogen substituted phenyl group. In specific embodiments, the phenyl group of $R_7$ is substituted with 1-5 halogens, including 1-3 chlorines, 1-3, fluorines, 1-5 fluorines, 1-2 bromines or 1-2 iodines. In specific embodiments, the phenyl group of $R_7$ is substituted with one or two methyl or methoxy groups. In specific embodiments, the phenyl group of $R_7$ is substituted with one or two nitro, azide, cyano, isocyano or thiocyano groups. In specific embodiments, $R_7$ is an optionally substituted benzyl group. In specific embodiments, $R_7$ is a substituted benzyl group. In specific embodiments, $R_7$ is a p-halogen substituted benzyl group. In specific embodiments, the benzyl group of $R_7$ is substituted with 1-5 halogens, including 1-3 chlorines, 1-3, fluorines, 1-5 fluorines, 1-2 bromines or 1-2 iodines on the phenyl ring. In specific embodiments, the benzyl group of $R_7$ is substituted with one or two methyl or methoxy groups on the phenyl ring. In specific embodiments, the benzyl group of $R_7$ is substituted with one or two nitro, azide, cyano, isocyano or thiocyano groups on the phenyl ring. In specific embodiments, $R_7$ is an optionally substituted phenethyl group. In specific embodiments, $R_7$ is a substituted phenethyl group. In specific embodiments, $R_7$ is a p-halogen substituted phenethyl group. In specific embodiments, the phenethyl group of $R_7$ is substituted with 1-5 halogens, including 1-3 chlorines, 1-3, fluorines, 1-5 fluorines, 1-2 bromines or 1-2 iodines on the phenyl ring. In specific embodiments, the phenethyl group of $R_7$ is substituted with one or two methyl or methoxy groups on the phenyl ring. In specific embodiments, the benzyl group of $R_7$ is substituted with one or two nitro, azide, cyano, isocyano or thiocyano groups on the phenyl ring.

Certain compounds useful in the methods of this invention are available from commercial sources. Novel compounds of the invention can be prepared by one of ordinary skill in the art employing synthetic methods that are well-known in the art or by routine adaptation of such methods from starting material and reagents that are available commercially or readily prepared by well-known methods. Schemes 1 and 2 illustrate exemplary synthetic schemes by which compounds of formulas I and II can be prepared from available starting materials by known methods. Methods useful in the preparation of compounds of the invention of formulas I and II can be found in the following references each of which is incorporated by reference herein in its entirety for the synthetic methods therein:

Dhindsa, G. S.; Vaid, R. K. (1986) Synthesis and mass spectral studies of some 3-alkyl-6-aryl-7-carbethoxy/carboxy-methyl-s-triazolo[3,4-b][1,3,4]thiadiazines Indian Journal of Chemistry, Section B: Organic Chemistry Including Medicinal Chemistry 25B(3), 283-7; Mazzone, G.; Bonina, F et al. (1989) Carboxymethyl- and carboxy-derivatives of 7H- and 5H-1,2,4-triazolo[3,4-b][1,3,4]thiadiazine: synthesis and biological evaluation Farmaco 44(10), 933-44.; Jakhar, A., Makrandi, J. K. (2012) Molecular iodine mediated one step synthesis and antibacterial properties of some 3-aryl-6-(6-substituted-4-methylcinnolin-3-yl)-7H-1,2,4-triazolo[3,4-b][1,3,4]thiadiazines Indian Journal of Chemistry, Section B: Organic Chemistry Including Medicinal Chemistry 51B(1), 313-317; Aytac, S. P; Tozkoparan, B, Kaynak, et al. (2009) Synthesis of 3,6-disubstituted 7H-1,2,4-triazolo[3,4-b]-1,3,4-thiadiazines as novel analgesic/anti-inflammatory compounds European Journal of Medicinal Chemistry 44(11), 4528-4538; WO 2009089027 A1 20090716; El-Serwy W. S. et al. (2013) Res. Chem. Intermed. 39:2543-2554; and Vovk, M. et al. (2010) Molecules 15:997-1006

The invention provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote. In a specific embodiment, the inhibition of UGM is in vivo in a nematode.

The invention also provides a method for inhibiting the growth of a microorganism containing UGM by contacting the microorganism with an amount of one or more of the compounds of any of the formulas herein effective for inhibiting the growth of the microorganism. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention also provides a method for attenuating the virulence of a microorganism containing UGM by contacting the microorganism with an amount of one or more of the compounds of any of the formulas herein effective for attenuating virulence of the microorganism. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention also provides a method for inhibiting the growth of a microorganism containing UGM by contacting the microorganism with an amount of one or more of the compounds of any of the formulas herein effective for inhibiting UGM. In a specific embodiment, the microorganism is a human or veterinary pathogen. In a specific embodiment, the microorganism is a bacterium. In another embodiment, the microorganism is of the genus *Mycobacterium*. In more specific embodiments, the microorganism is *Mycobacterium tuberculosis* or *Mycobacterium smegmatis*. In another embodiment, the microorganism is of the genus *Klebsiella*, including *Klebsiella pneumoniae*. In other embodiments, the microorganism is a prokaryote or a eukaryote.

The invention further provides a method of treating a human, a non-human mammal or a non-human animal individual having or believed to have an infection of a microorganism containing UGM by administering to the individual an amount of one or more compounds of any of the formulas herein effective for inhibiting the growth of the microorganism. In specific embodiments, the microorganism is a bacterium or a *mycobacterium*. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis, Mycobacterium smegmatis* or *Klebsiella pneumoniae*. The pathogenic microorganism can be a prokaryote or a eukaryote.

The invention additionally provides a method for treating a human, a non-human mammal or a non-human animal individual having or believed to have an infection of a microorganism containing UGM by administering an effective amount of a compound of this invention of any of the formulas herein, in combination with an antibiotic or antiparasitic agent appropriate for treatment of the infection. Compounds of this invention can enhance the effectiveness of art-known antibiotics and are useful in combination therapy in addition to such antibiotics. The compounds of the present invention can, for example, be employed in combination therapy with antibiotics, such as ethambutol, isoniazid, rifampicin, and pyrazinamide. Such combination therapy is particularly useful in the treatment of mycobacterial infections.

The invention further provides a method of treating a human, a non-human mammal or a non-human animal individual having or believed to have an infection of a parasitic pathogen containing UGM by administering to the individual an amount of one or more compounds of any of the formulas herein effective for inhibiting the growth of the parasitic pathogen. In specific embodiments, the parasitic pathogen is a protozoan or a nematode. In a related embodiment, the treatment method includes administering an effective amount of a compound of this invention of any of the formulas herein, in combination with antiparasitic agent appropriate for treatment of the infection. The compounds of the present invention can, for example, be employed in combination therapy with antiparasitic agent, particularly anthelminthic agents, such as diethylcarbamazine, teracyclies, rifampicin, chloramphenicol, alendazole, mebendazole, levamisole, pyrantel and ivermectic or combinations of two or more thereof. Such combination therapy is particularly useful in the treatment of nematode infections.

The invention additional provides a medicament comprising one or more compounds of the formulas herein effective for inhibiting the growth of a microorganism, including a eukaryotic parasite, or effective for attenuating the virulence of a microorganism, including a eukaryotic parasite, which contains UGM. The invention additional provides a medicament comprising one or more compounds of any of the formulas herein effective for inhibiting UGM. In specific embodiments, the microorganism is a bacterium or a *mycobacterium*. In specific embodiments, the microorganism is of the genus *Mycobacterium* or *Klebsiella*. In additional embodiments, the microorganism is *Mycobacterium tuberculosis, Mycobacterium smegmatis* or *Klebsiella pneumoniae*. In additional embodiments, the invention provides a medicament comprising one or more compounds of the formulas herein effective for inhibiting the growth of a protozoan or effective for attenuating the virulence of a protozoan which contains UGM. The invention additional provides a medicament comprising one or more compounds of any of the formulas herein effective for inhibiting UGM of a protzoan. In specific embodiments, the protozoan are among others. Plasmodium, Trypanosomes and *Leishmania*. In additional embodiments, the invention provides a medicament comprising one or more compounds of the formulas herein effective for inhibiting the growth of a nematode or effective for attenuating the virulence of a nematode which contains UGM. The invention additional provides a medicament comprising one or more compounds of any of the formulas herein effective for inhibiting UGM of a nematode. Nematode include among others, *Ancylostoma, Necator, Ascaris, Strongyloides, Trichinella, Capillaria, Toxocara, Toxascaris, Trichuris, Enterobius, Onchocerca, Brugia, Wuchereria*, or *Dracunculus*.

The invention also provides a method of making a medicament for treating an individual (human, mammal or animal) having a bacterial or mycobacterial infection. In specific embodiments, the mycobacterial infection is tuberculosis. In specific embodiments, the microorganism is of the genus *Mycobacterium* or *Klebsiella*. In additional embodiments, the microorganism is *Mycobacterium tuberculosis, Mycobacterium smegmatis* or *Klebsiella pneumoniae*. In a specific embodiment, the method of making a medicament includes the step of combining an amount of a compound of any of the formulas herein with a pharmaceutically effective carrier. In a specific embodiment, the medicament is in a dosage form appropriate for oral administration, topical administration or administration by injection.

In specific embodiments, the invention also provides compounds of any of the formulas herein which inhibit the growth of a microorganism having UGM which exhibit a dissociation constant K for the UGM enzyme of 100 µM or less. In another embodiment, the compound exhibits a dissociation constant K for the UGM enzyme of 50 µM or less. In another embodiment, the compound exhibits a dissociation constant K for the UGM enzyme of 25 µM or less. In another embodiment, the compound exhibits a dissociation constant K for the UGM enzyme of 10 µM or less. In further embodiments, the microorganism is a *Mycobacterium*, particularly *Mycobacterium tuberculosis*. In additional embodiments the microorganism is of the genus *Klebsiella*.

In specific embodiments, the invention provides compound of any formulas herein which exhibit Kd (µM) on $UGM_{myco}$ of 100 or less. In other embodiments, the invention provides compound of any formulas herein which exhibit Kd (µM) on $UGM_{myco}$ of 80 or less. In other embodiments, the invention provides compound of any formulas herein which exhibit Kd (µM) on $UGM_{myco}$ of 60 or less. In other embodiments, the invention provides compounds of any formulas herein which exhibits exhibit Kd (µM) as measured by the fluorescence polarization assay on the UGM isoform from *M. tuberculosis* of 25 or less.

In specific embodiments, the invention provides compounds of any formulas herein which exhibit Kd (µM) as measured by the fluorescence polarization assay on the UGM isoform from *K. pneumoniae* of 80 or less. In other embodiments, the invention provides compounds of any formulas herein which exhibit Kd (µM) as measured by the fluorescence polarization assay on the UGM isoform from *K. pneumoniae* of 60 or less. In other embodiments, the invention provides compounds of any formulas herein which exhibit Kd (µM) as measured by the fluorescence polarization assay on the UGM isoform from *K. pneumoniae* of 25 or less.

The invention further provides a method for inhibiting UGM in vitro or in vivo by contacting a biological composition comprising an active UGM with an amount of one or more of the compounds of any of the formulas herein effective for inhibiting UGM. In a specific embodiment, the inhibition of UGM is in vivo in a prokaryote. In a specific embodiment, the inhibition of UGM is in vivo in a eukaryote.

Compounds of the invention are useful for inhibiting the growth of a microorganism containing UGM which is the enzyme responsible for the conversion of UDP-galactopyranose to UDP-galactofuranose. UGM is expected to be present in microorganisms in which galactofuranose (Galf) residues are present, for example in cell walls. Galactofuranose (Galf) residues are present in many pathogenic microorganisms (Pedersen, L. L.; Turco, S. J. Cell. Mol. Life Sci. 2003, 60, 259-266.) The gene encoding UGM is essential for mycobacterial viability (Pan, F.; Jackson, M.; Ma, Y. F.; McNeil, M. J. Bacteriol. 2001, 183, 3991-3998) suggesting that Galf-containing glycoconjugates are necessary components of the mycobacterial cell wall. Compounds of the invention are useful for inhibiting the growth of microorganisms containing galactofuranose residues, particularly those having such residues in the cell wall and more particularly pathogenic microorganisms containing galactofuranose residues.

Compounds of the invention are useful for inhibition of growth of microorganisms of the genus *Mycobacterium*, particularly including *M. tuberculosis* and *M. smegmatis*. Compounds of the invention can also be employed to inhibit the growth of *Mycobacterium leprae*, *Mycobacterium bovis*, *Mycobacterium africanum*, *Mycobacterium canetti*, and *Mycobacterium microti*.

Compounds of the invention are useful for inhibition of the growth of Gram-negative bacteria and particularly those of the genus *Klebsiella* and particularly *K. pneumoniae*. The compounds of the invention can also be employed to inhibit the growth of *Klebsiella ozaenae*, *Klebsiella rhinoscleromatis*, *Klebsiella oxytoca*, *Klebsiella planticola*, *Klebsiella terrigena*, and *Klebsiella ornithinolytica*. Klebsiellae are important pathogens in nosocomial infections. The compounds of the invention are useful for the treatment of nosocomial infections.

Compounds of the invention are useful for inhibition of the growth of or for attenuation of the virulence of eukaryotic pathogens, including yeast, fungi, protozoa and nematodes. The compounds of the invention are useful for inhibiting the growth or attenuating the virulence of, for example, pathogenic *Aspergillus*, in particular *Aspergillus fumagatus*.

The term "microorganism" is used broadly herein to refer to organisms too small to be seen with the naked human eye and includes prokaryotes (e.g., bacteria and mycobacteria), single cell and multiple cell eukaryotes, yeast, fungi and protozoa. More specifically microorganisms upon which the compounds of this invention act are human or non-human mammal pathogens. Pathogenic protozoa include, among others, Plasmodium, Trypanosomes and *Leishmania* (e.g., *Leishmania major, Trypanosoma cruizii*.) Fungi include *Cryptococcus* (e.g., *Cryptococcus neoformans*). Microorganism also includes parasitic nematodes.

Animals (including fish and birds) and humans are subject to infection by nematodes which can result in debilitation long term disease. Infection by nematodes can result in significant economic loss in domestic animals and poultry. Infection may be in the gastrointestinal tract, the lymphatic system or in other tissue or organs. Nematode parasites include, among others, *Ancylostoma, Necator, Ascaris, Strongyloides, Trichinella, Capillaria, Toxocara, Toxascaris, Trichuris, Enterobius, Onchocerca, Brugia, Wuchereria*, or *Dracunculus*. More specifically, nematode parasites include among others *Ancylostoma duodenale, Necator americanus, Trichuris trichiura, Ascaris lumbricoides, Strongyloides stercoralis, Trichinella spiralis, Toxocara canis, Toxocara cati, Enterobius vermicularis, Onchocerca volvulus, Brugia malayi, Brugia timori, Wuchereria bancrofti*, and *Drancunculus medinensis*. Diseases associated with nematode infection include filariasis (lymphatic filariasis, subcutaneous filariasis and serous cavity filariasis), various GI tract infections (hookworm, roundworm, pinworm, whipworm, thread worm), Toxocariasis, Trichinosis, Onchocerciasis (River Blindness).

In a specific embodiment, compounds of this invention of any of the formulas herein can block incorporation of Galf into polysaccharides essential for viability or virulence of pathogenic microorganisms.

In specific embodiments, the invention provides compounds of any formulas herein which are cell permeable.

The term "alkyl" refers to a monoradical of a branched or unbranched (straight-chain or linear) saturated hydrocarbon. Alkyl groups include those having 1 to 22 carbon atoms (C1-C22 alkyl). Alkyl groups include those having 1-12 carbon atoms (C1-C12 alkyl). Alkyl groups include those having 1 to 6 carbon atoms (C1-C6 alkyl) including methyl, ethyl, propyl, butyl, pentyl and hexyl groups, including all isomers thereof. In specific embodiments, alkyl groups include those having 1-3 carbons (C1-C3 alkyl groups). The term "cycloalkyl" refers to cyclic alkyl groups having 3 to 22, preferably 5-10 carbon atoms and more preferably 5 or 6 carbon atoms. Cycloalkyl groups can have a single ring, may be bicyclic, tricyclic or the like. Cycloalkyl groups include, by way of example, single ring structures such as cyclopropyl, cyclobutyl, cyclopentyl, cyclohexyl, cyclooctyl, and the like, or multiple ring structures such as adamantanyl, and the like. Unless otherwise indicated alkyl groups including cycloalkyl groups are optionally substituted as defined herein.

The term "alkylene" refers to a diradical of a branched or unbranched saturated hydrocarbon chain, which unless otherwise indicated can have 1 to 10 carbon atoms, 1 to 6 carbon atoms, or 2-4 carbon atoms. This term is exemplified by groups such as methylene (—$CH_2$—), ethylene (—$CH_2CH_2$—), and more generally —$(CH_2)n$, where n is 1-10 or more preferably 1-6 or n is 1, 2, 3 or 4. Alkylene groups may be branched, e.g., by substitution with alkyl group substituents. Alkylene groups may be optionally substituted as described herein.

The term alkoxy refers to the group —OR' where R' is an alkyl group as defined above.

A specific substituted alkyl group is an aryl substituted alkyl group where the terms aryl and alkyl are as defined herein. In specific embodiments, the substituted alkyl group is a C1-C3 alkyl group, and in particular is a methyl group. In specific examples the aryl group is an optionally substituted phenyl group. In specific examples, these groups include optionally substituted benzyl groups and optionally substituted phenethyl groups.

Another specific substituted alkyl group is a halo substituted alkyl group where alkyl is as defined above. This group includes alkyl groups having 1-3 carbon atoms and having 1 to 7 halogens. This group particularly includes alkyl groups with fluorine substitution, chlorine substitution and bromine substitution. A specific haloalkyl group is —$CF_3$.

The term "alkenyl" refers to a monoradical of a branched or unbranched (straight-chain or linear) hydrocarbon having one or more C—C double bonds (C═C). Alkenyl groups include those having 2 to 22 carbon atoms (C2-C22 alkenyl). Alkenyl groups include those having 1-12 carbon atoms (C2-C12 alkenyl). Alkenyl groups include those having 1 to 6 carbon atoms (C2-C6 alkenyl) including ethenyl, propenyl, butenyl, pentenyl and hexyenyl groups, including all isomers thereof. In specific embodiments, alkenyl groups include those having 2 or 3 carbons (C2-C3 alkenyl groups). The term "cycloalkenyl" refers to cyclic alkenyl groups having 3 to 22, preferably 5-10 carbon atoms and more preferably 5 or 6 carbon atoms and one or more C—C double bonds. Cycloalkenyl groups can have a single ring, may be bicyclic, tricyclic or the like. Cycloalkenyl groups include, by way of example, single ring structures such as cyclopropenyl, cyclobutenyl, cyclopentenyl, cyclohexenyl, cyclooctenyl, and the like, or multiple ring structures such as adamantanenyl, and the like. Unless otherwise indicated alkenyl groups including cycloalkenyl groups are optionally substituted as defined herein. In preferred embodiments, alkenyl groups have one or two C—C double bonds which may be conjugated. In specific embodiments, alkenyl groups and cycloalkenyl groups have a single C—C double bond.

The term "carbocyclic" is used generically herein to refer to groups which contain a carbon ring which may be a saturated, partially unsaturated or aromatic ring. Carbocyclic groups may contain one or more than one carbon ring which ring may be a cycloakyl, unsaturated cycloalkyl or aryl ring. Typically carbocyclic rings include those having 3-12 carbon atoms in the ring. Carbocyclic rings include those having two or more fused rings, bicyclic rings, tricyclic ring etc. Preferred carbocyclic rings have 6 to 12 carbon atoms. Unless otherwise indicated carbocyclic groups are optionally substituted as defined herein.

The term "heterocyclyl" is also used generically herein to refer to carbocyclic rings in which one or more ring carbons are replaced with a heteroatom. The heterocyclyl ring may contain a carbon ring in combination with a heteroatom containing ring. Heterocyclyl groups can contain from one to six heteroatoms including one, two, three or four hetero atoms. Preferred heteroatoms are N, O or S (or NR' where R' is a hydrogen or an optional substituent). Heterocyclyl groups can be or contain heteroaryl groups. Unless otherwise indicated heterocyclyl groups are optionally substituted as defined herein. Heterocyclyl groups include those having 5-12 ring atoms, with 1, 2 or 3 heteroatoms and 1, 2 or 3 double bonds. Heterocyclyl groups include those having 5- and 6-member rings with one or two nitrogens and one or two double bonds. Heterocyclyl groups include those having 5- and 6-member rings with an oxygen or a sulfur and one or two double bonds. Heterocyclyl groups include those having 5- or 6-member rings and two different heteroatom, e.g., N and O, O and S or N and S. Specific heterocyclyl groups include among others among others, pyrrolidinyl, piperidyl, piperazinyl, pyrrolinyl, morpholinyl, oxazolyl, oxazolinyl, oxazolidinyl, indolyl, triazoly, and triazinyl groups.

The term "heterocyclyoxy" refers to the group —OR', where R' is an heterocyclyl group as defined above.

The term "aryl" refers to a monoradical containing at least one aromatic ring. The radical is formally derived by removing a H from a ring carbon. Aryl groups contain one or more rings at least one of which is aromatic. Rings of aryl groups may be linked by a single bond or a linker group or may be fused. Exemplary aryl groups include phenyl, biphenyl and naphthyl groups. Aryl groups include those having from 6 to 30 carbon atoms. Preferred aryl groups are those containing 6-12 carbon atoms. Unless otherwise noted aryl groups are optionally substituted as described herein.

The term aryoxy refers to the group —OR', where R' is an aryl group as defined

The term "heteroaryl" refers to a group that contains at least one aromatic ring in which one or more of the ring carbons is replaced with a heteroatom (non-carbon atom). To satisfy valence the heteroatom may be bonded to H or a substituent groups. Ring carbons may be replaced with —O—, —S—, —NR—, —N═, —PR—, or —POR— among others, where R is an alkyl, aryl, heterocyclyl or heteroaryl group. Heteroaryl groups may include one or more aryl groups (carbon aromatic rings) heteroaromatic and aryl rings of the heteroaryl group may be linked by a single bond or a linker group or may be fused. Heteroaryl groups include those having aromatic rings with 5 or 6 ring atoms of which 1-3 ring atoms are heteroatoms. Preferred heteroatoms are —O—, —S—, —NR— and —N═. Heteroaryl groups include those containing 5-12 ring atoms as well as those having 5 and 6 ring atoms. Unless otherwise noted heteroaryl groups are optionally substituted as described herein. Heteroaryl groups include groups having one or more aromatic rings in which at least one ring contains a heteroatom (a non-carbon ring atom). Heteroaryl groups include those having one or two heteroaromatic rings carrying 1, 2 or 3 heteroatoms and optionally have one 6-member aromatic ring. Heteroaryl groups can contain 5-20, 5-12 or 5-10 ring atoms. Heteroaryl groups include those having one aromatic ring contains a heteroatom and one aromatic ring containing carbon ring atoms. Heteroaryl groups include those having one or more 5- or 6-member aromatic heteroaromatic rings and one or more 6-member carbon aromatic rings. Heteroaromatic rings can include one or more N, O, or S atoms in the ring. Heteroaromatic rings can include those with one, two or three N, those with one or two O, and those with one or two S, or combinations of one or two or three N, O or S. Specific heteroaryl groups include furyl, thienyl, pyrrolyl, imidazolyl, pyrazolyl, pyridinyl, pyrazinyl, pyrimidinyl, quinolinyl, and purinyl groups.

The term heteroaryoxy refers to the group —OR', where R' is a heteroaryl group as defined Unless otherwise specified optional substitution means substitution by one or more non-hydrogen substituents selected from halogen, hydroxyl, amine, cyano, azide, nitro, isocyanate, isothiocyanate, C1-C6 alkyl, C1-C3 alkyl, C1-C6 haloalkyl, C1-C3 haloalkyl, phenyl, benzyl, sulfate, phosphate, phosphonate, carboxyl, sulfonyl, sulfonamide, and amide. All alkyl, aryl, heteroaryl, heterocyclyl, carbocyclic groups herein are optionally substituted with one or more non-hydrogen substituents unless otherwise specified. Substitution may be on one or more carbons or, if feasible, on one or more heteroatoms, e.g., a nitrogen. The number of substituents on such groups depends generally upon the nature of the group, but includes substitution with one, two, three, four, five or six substituents.

As to any of the groups herein which contain one or more substituents, it is understood, that such groups do not contain any substitution or substitution patterns which are sterically impractical and/or synthetically non-feasible. In addition, the compounds of this invention include all stereochemical isomers arising from the substitution of these compounds.

The compounds of this invention may contain one or more chiral centers. Accordingly, this invention is intended to include racemic mixtures, diasteromers, enantiomers and mixture enriched in one or more stereoisomer. The scope of the invention as described and claimed encompasses the racemic forms of the compounds as well as the individual enantiomers and non-racemic mixtures thereof.

Treatment methods of this invention comprise the step of administering an effective amount of one or more compounds of this invention, or a salt thereof to an individual (human and/or non-human animal) to treat or prevent infection. The term "effective amount," as used herein, refers to the amount of the compound, that, when administered to the individual is effective to at least partially treat or prevent infection, or to at least partially ameliorate a symptom of infection. Infection herein refers to infection by a microorganism which contains the enzyme UGM. Infection herein refers to infection by a fungus, algae, bacterium or nematode. Infection herein refers to infection by a *mycobacterium*. As is understood in the art, the effective amount of a given compound will depend at least in part upon, the type of infectious organism, the mode of administration, any carrier or vehicle (e.g., solution, emulsion, etc.) employed, the extent of damage and the specific individual to whom the compound is to be administered (age, weight, condition, sex, etc.). The dosage requirements needed to achieve the "effective amount" vary with the particular compositions employed, the route of administration, the severity of the symptoms presented and the particular subject being treated. Based on the results obtained in standard pharmacological test procedures, projected daily dosages of active compound can be determined as is understood in the art.

Compounds of this invention can be employed in unit dosage form, e.g. as tablets or capsules. In such form, the active compound or more typically a pharmaceutical composition containing the active compound is sub-divided in unit dose containing appropriate quantities of the active compound; the unit dosage forms can be packaged compositions, for example, packaged powders, vials, ampoules, pre-filled syringes or sachets containing liquids. The unit dosage form can be, for example, a capsule or tablet itself, or it can be the appropriate number of any such compositions in package form.

Any suitable form of administration can be employed in the method herein. The compounds of this invention can, for example, be administered in oral dosage forms including tablets, capsules, pills, powders, granules, elixirs, tinctures, suspensions, syrups and emulsions. Oral dosage forms may include sustained release or timed release formulations. The compounds of this invention may also be administered topically, intravenously, intraperitoneally, subcutaneously, or intramuscularly, all using dosage forms well known to those of ordinary skill in the pharmaceutical arts.

Pharmaceutical and veterinary compositions of the invention may also be in the form of oil-in-water or water-in-oil emulsions, where the oily phase is any suitable oil, including vegetable or mineral oil. Emulsifying agents and/or surfactants may be included in such emulsions. In an embodiment, the compositions of the invention are formed as microemulsions. Methods and materials for formation of emulsions and microemulsions for pharmaceutical and veterinary compositions are well known in the art.

Pharmaceutical and veterinary compositions of the invention may be in the form of aqueous solution or aqueous suspensions where the active ingredient is dissolved or dispersed, typically in the form of a powder, in an aqueous pharmaceutically acceptable solvent. Alternatively, active ingredients can be dispersed in an oily phase.

In another embodiment, the pharmaceutical and veterinary compositions of the can be in the form of pastes, gels and creams, wherein the active ingredient is dissolved in a component of the paste, gel or cream or is dispersed therein.

The therapeutically active compounds of the invention can be administered alone, but generally will be administered with a pharmaceutical carrier selected upon the basis of the chosen route of administration and standard pharmaceutical practice.

Pharmaceutical compositions and medicaments of this invention comprise one or more compounds in combination with a pharmaceutically acceptable carrier, excipient, or diluent. Such compositions and medicaments are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety.

Pharmaceutically acceptable carriers are those carriers that are compatible with the other ingredients in the formulation and are biologically acceptable. Carriers can be solid or liquid. Solid carriers can include one or more substances that can also act as flavoring agents, lubricants, solubilizers, suspending agents, fillers, glidants, compression aids, binders, tablet-disintegrating agents, or encapsulating materials. Liquid carriers can be used in preparing solutions, suspensions, emulsions, syrups and elixirs. The active ingredient can be dissolved or suspended in a pharmaceutically acceptable liquid carrier such as water (of appropriate purity, e.g., pyrogen-free, sterile, etc.), an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Compositions for oral administration can be in either liquid or solid form.

The compounds of the present inventions may form salts which are also within the scope of this invention. Reference to a compound of the formulas herein is understood to include reference to salts thereof, unless otherwise indicated. The term "salt(s)", as employed herein, denotes acidic and/or basic salts formed with inorganic and/or organic acids and bases. In addition, when a compound of a formula herein contains both a basic moiety, such as, but not limited to an amine or a pyridine ring, and an acidic moiety, such as, but not limited to, a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Compounds of the present invention, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore exist in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

Well-known methods for assessment of drugability can be used to further assess active compounds of the invention for application to given therapeutic application. The term "drugability" relates to pharmaceutical properties of a prospective drug for administration, distribution, metabolism and excretion. Drugability is assessed in various ways in the art. For example, the "Lipinski Rule of 5" for determining drug-like characteristics in a molecule related to in vivo absorption and permeability can be applied (C. A. Lipinski, F. Lombardo, B. W. Dominy, P. J. Feeney, Experimental and computational approaches to estimate solubility and permeability in drug discovery and development settings, Adv. Drug Del. Rev., 2001, 46, 3-26 and Arup K. Ghose, Vellarkad N. Viswanadhan, and John J. Wendoloski, A Knowledge-Based Approach in Designing Combinatorial or Medicinal Chemistry Libraries for Drug Discovery, J. Combin. Chem., 1999, 1, 55-68.)

In general a preferred drug for oral administration exhibits no more than one violation of the following rules:
(1) Not more than 5 hydrogen bond donors (e.g., nitrogen or oxygen atoms with one or more hydrogens);
(2) Not more than 10 hydrogen bond acceptors (e.g., nitrogen or oxygen atoms);
(3) Molecular weight under 500 g/mol and more preferably between 160 and 480; or
(4) log P less than 5 and more preferably between −0.4 to +5.6 and yet more preferably −1<log P<2. Methods for calculating or experimentally determining log P are well-known in the art. Compounds of this invention preferred for therapeutic application include those that do not violate one or more of 1-4 above.

Compounds of this invention preferred for therapeutic application include those having log P less than 5 and more preferably between −0.4 to +5.6 and yet more preferably −1<log P<2.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. A number of specific groups of variable definitions have been described herein. It is intended that all combinations and subcombinations of the specific groups of variable definitions are individually included in this disclosure.

Compounds described herein may exist in one or more isomeric forms, e.g., structural or optical isomers. When a compound is described herein such that a particular isomer, enantiomer or diastereomer of the compound is not specified, for example, in a formula or in a chemical name, that description is intended to include each isomers and enantiomer (e.g., cis/trans isomers, R/S enantiomers) of the compound described individual or in any combination.

Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Isotopic variants, including those carrying radioisotopes, may also be useful in diagnostic assays and in therapeutics. Methods for making such isotopic variants are known in the art.

Specific names of compounds are intended to be exemplary, as it is known that one of ordinary skill in the art can name the same compounds differently.

Molecules disclosed herein may contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated. The invention illustratively described herein suitably may be practiced in the absence of any element or elements, limitation or limitations which is not specifically disclosed herein.

It is understood that this invention is not limited to the particular methodology, protocols, cell lines, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

THE EXAMPLES

Screening

The Protein Data Bank contains several UGM crystal structures; however, only two present a bacterial UGM poised for catalysis and complexed with the UDP-Galp substrate. Of these, the structure of substrate-bound K. pneumoniae UGM (KpUGM) (PDB ID: 3INT) [Gruber, T. D., et al., X-ray crystallography reveals a reduced substrate complex of UDP-galactopyranose mutase poised for covalent catalysis by flavin. Biochemistry, 2009. 48(39): p. 9171-3] was chosen as the starting point for virtual screening with DOCK. In this structure, the enzyme is in the active form, with the flavin adenine dinucleotide (FAD) cofactor reduced and a flexible loop (residues 166-178) closed over the active site.

In order to evaluate different sampling parameters for the docking, a set of 1,700 property matched decoys [Mysinger, M. M., et al., Directory of useful decoys, enhanced (DUD-E): better ligands and decoys for better benchmarking. J Med Chem, 2012. 55(14): p. 6582-94] for a set of known binders from the 2-aminothiazole (AT) (n=25) [Dykhuizen et al. 2008] and thiazolidinones TZ (n=13) [Dykhuizen et al. 2008; Carlson et al. 2006] scaffolds (FIG. 7) was created. The decoys and known binders were docked and the adjusted logAUC [Mysinger et al. 2010; Irwin, J. J., et al., ZINC: a free tool to discover chemistry for biology. J Chem Inf Model, 2012. 52(7): p. 1757-68] was assessed. LogAUC is a measure of the ability of docking to enrich for the known binders over decoys, which emphasizes early enrichment. A random ranking will yield a value of logAUC=0.

Figure 2A:
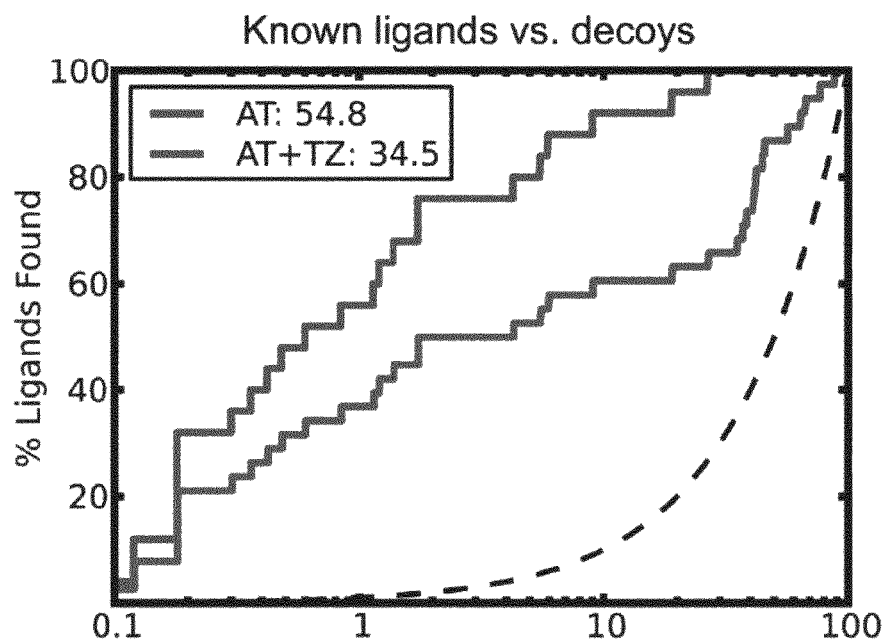
FIGS. 2A and B are LogAUC enrichment plots of known UGM inhibitors vs.

The optimal docking configuration led to a logAUC=34.5 for all 38 known binders and logAUC=54.8 when considering just ligands from the AT series (FIG. 2A). AT ligands exhibited much better docking scores than TZ ligands. TZ are well-documented pan-assay Interference compounds [Baell, J. B. and G. A. Holloway, New substructure filters for removal of pan assay interference compounds (PAINS) from screening libraries and for their exclusion in bioassays. J Med Chem, 2010. 53(7): p. 2719-40] and it has been proposed in the past that the TZ ligands actually bind to UGM via a covalent binding mechanism [Carlson et al. 2006]. This explains their poor performance in the docking.

Figure 2B:
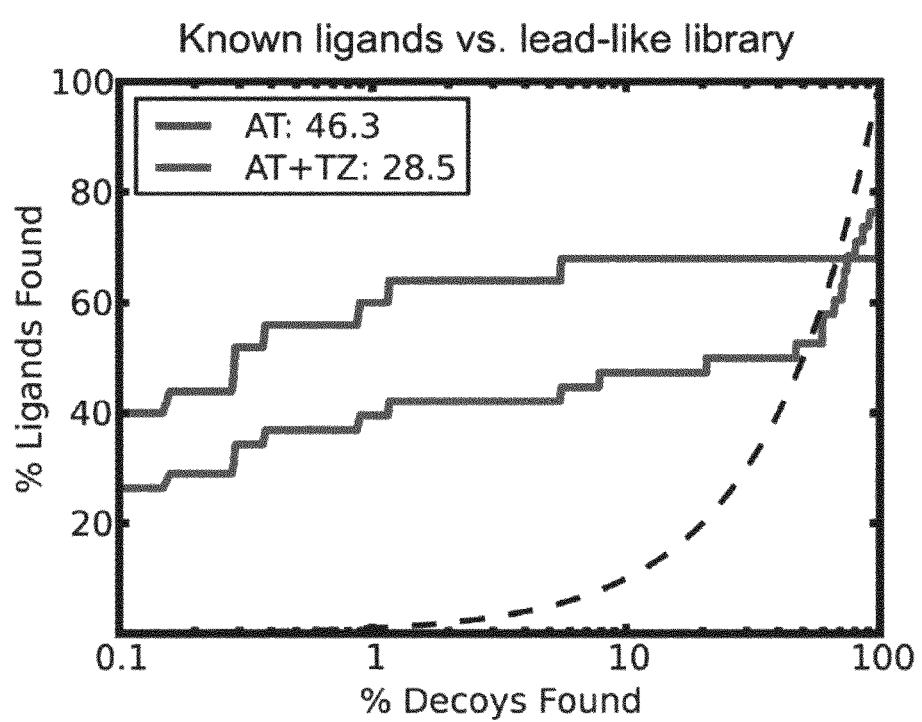

Using the same docking configuration, a library of 4.7 million lead-like molecules (250<molecular weight<350; x Log P≤3.5; number of rotatable bonds≤7 [Teague, S. J., et al., The Design of Leadlike Combinatorial Libraries. Angew Chem Int Ed Engl, 1999. 38(24): p. 3743-3748; Irwin et al. 2012]) were processed with DOCK against UGM. AT ligands showed very good enrichment against this much larger set as well, with logAUC=46.3 (FIG. 2B). This encouraged selection of potential inhibitors for experimental testing.

Figure 3A:
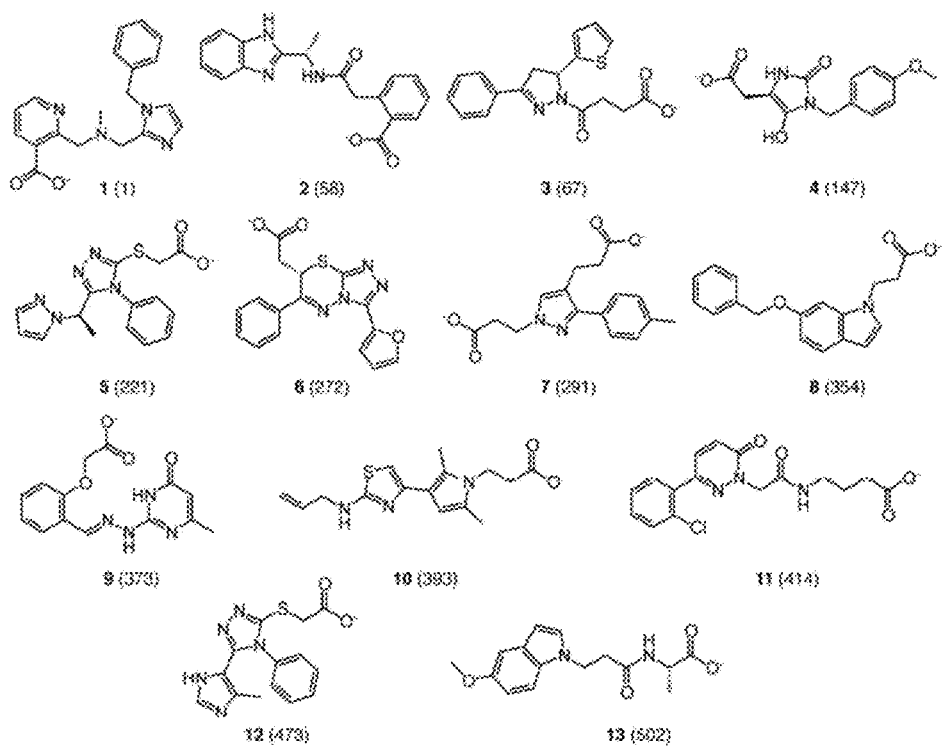
FIGS. 3A and B relate to in vitro analysis of predicted UGM inhibitors.

Thirteen of the 0.01% top-ranking molecules from the docking screen (FIG. 3A, provides structures) were manually selected for in vitro analysis. Criteria for selection included a negative charge for interaction with two catalytically crucial arginine residues in the UGM active site [Chad, J. M., et al., Site-directed mutagenesis of UDP-galactopyranose mutase reveals a critical role for the active-site, conserved arginine residues. Biochemistry, 2007. 46(23): p. 6723-32]. Additional orthogonal criteria that are omitted in the docking scoring function were also considered, such as probable protonation states, internal ligand strain, and chemical diversity.

Figure 3B:
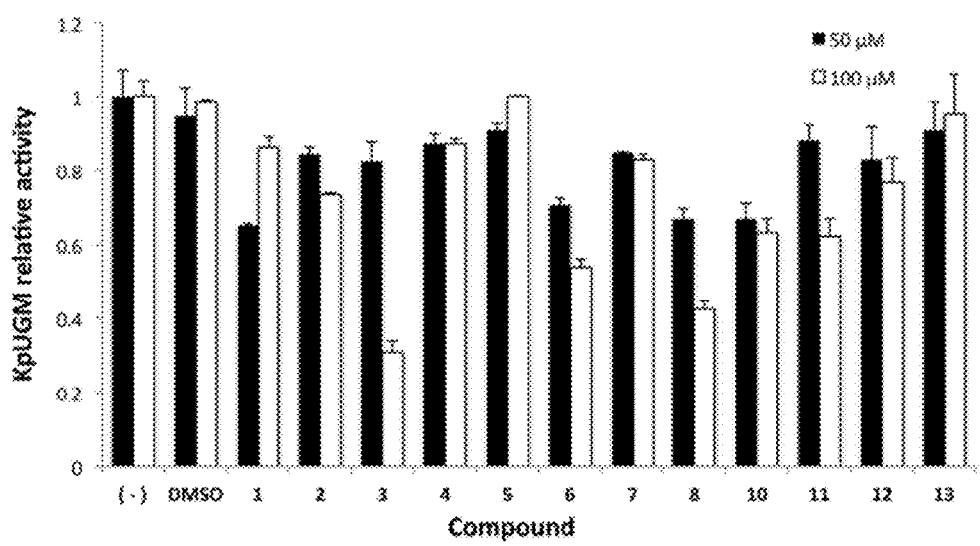
FIG. 3B is a graph of KpUGM activity monitored in the presence of predicted ligands via a discontinuous HPLC-based assay. Due to solubility issues molecule 9 could not be tested at these concentrations.
Figure 8:
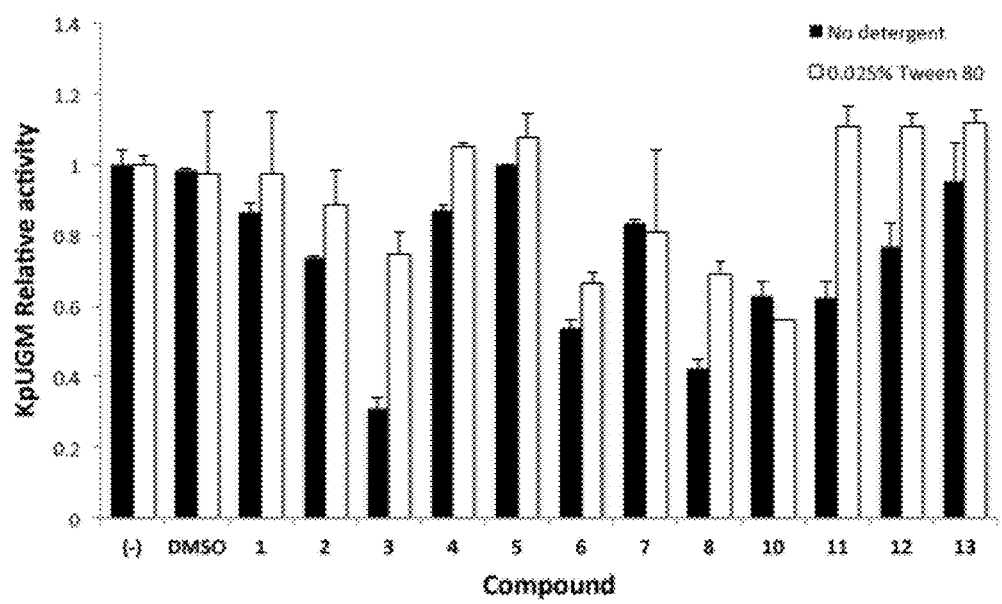
FIG. 8 is a graph showing the effect of detergent on UGM inhibition by docking molecules. Docking compounds were tested at 100 µM for KpUGM inhibition in the presence and absence of 0.025% Tween 80. Compounds 6 and 10 appeared insensitive to detergent.

A high pressure liquid chromatography (HPLC) based assay [Lee, R., et al., Enzymatic Synthesis of UDP-Galactofuranose and an Assay for UDP-Galactopyranose Mutase Based on High-Performance Liquid Chromatography. Anal Biochem, 1996: p. 1-7] was used to monitor inhibition of UGM activity by the 13 selected molecules (FIG. 3B). At 100 μM, six molecules showed more than 25% inhibition of KpUGM activity. Five of these molecules showed dose-dependent inhibition, ranging 15-33% inhibition at 50 μM. To eliminate aggregation-based non-specific inhibition [McGovern, S. L., et al., A common mechanism underlying promiscuous inhibitors from virtual and high-throughput screening. J Med Chem, 2002. 45(8): p. 1712-22] we repeated the assay in the presence of detergent (0.025% Tween 80). Three of the 13 compounds were sensitive to detergent, showing reversal of inhibition (FIG. 8) and were not further considered.

Compounds 6 and 10 were selected as the two most promising inhibitors. Dynamic light scattering (DLS) indicated that these compounds do not form detectable colloids at 100 μM (FIGS. 9A-9G 3). Additionally, they do not display any inhibition of AmpC β-lactamase, an unrelated hydrolase, at 100 μM. This gave confidence that the observed UGM inhibition was not an artifact of small molecule aggregation. Compounds 6 and 10 were then tested in the previously reported FP assay, inhibiting KpUGM with Kd(6)=62 μM and Kd(10)=9 μM, FIG. 10A and FIG. 10B respectively.

Figure 4A:
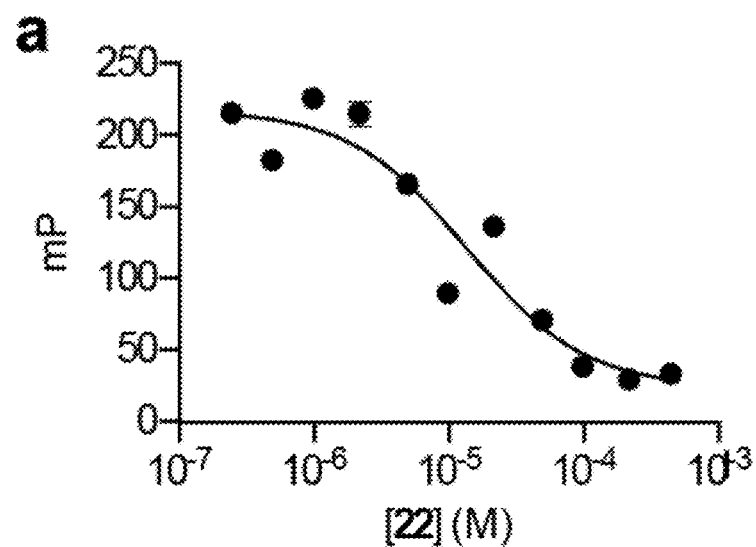
FIGS. 4A-F relate to correlation of competitive KpUGM inhibition by 22 and 30 with M. smegmatis cell-killing.
Figure 11A:
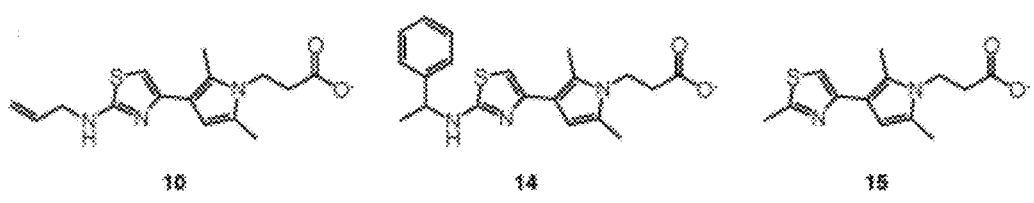
FIGS. 11A-C illustrate analogs of compound 10 having improved UGM inhibition. Structures are shown in FIG. 11A.
Figure 11B:
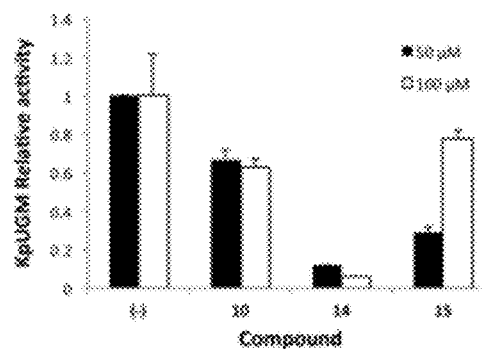
Figure 11C:
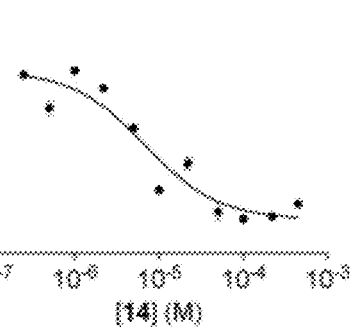
Figure 12:
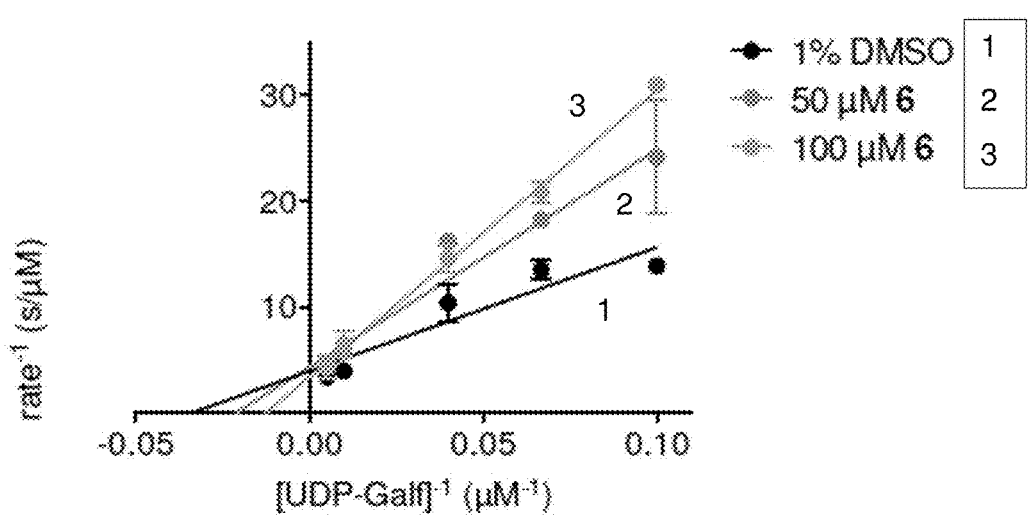
FIG. 12 illustrates Lineweaver Burk analysis of in vitro KpUGM inhibition by compound 6.
Figure 13A:
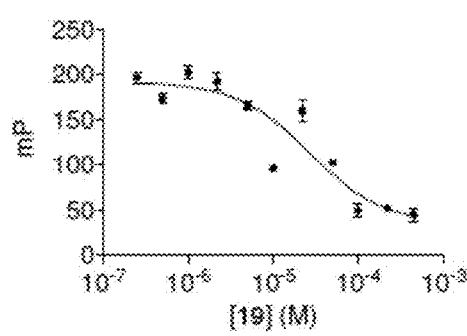
FIGS. 13A-B are graphs illustrating FP analysis of selected first generation compound 6 analogs. Compounds 19 (FIG. 13A) and 24 (FIG. 13B) displayed Kd values of 15 µM and 9.2 µM, respectively.
Figure 13B:
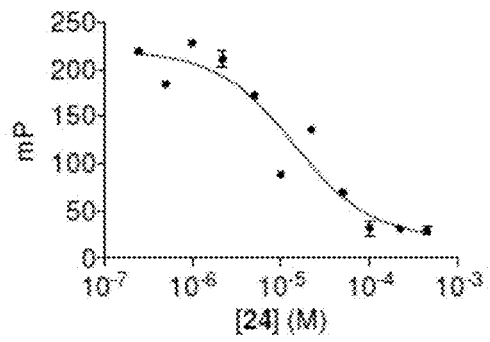

To study SAR of 6 and 10, commercially available analogs of the leads were purchased and tested. One analog of 10 (FIG. 11A shows structures of compounds 10, 14 and 18), i.e., compound 14, showed improved KpUGM inhibition (FIG. 11B), and slightly tighter binding than compound 10 (FIG. 11C). A lack of additional purchasable analogs as well as solubility issues further pursuing this series. Compound 6, on the other hand, had many commercially available analogs. Compound 6 displayed competitive inhibition of KpUGM in Lineweaver-Burk analysis with a $K_i$ of 78 μM (FIG. 12), similar to the $K_d$ value for 6 obtained in the FP assay. Eleven analogs of 6 were selected and sourced for testing. Eight analogs showed improved inhibition of KpUGM (FIG. 6) with up to 96%/88% inhibition at 100 μM/50 μM in the HPLC assay. The best performing molecules (19, 22, and 24) were also tested in the FP assay, displaying $K_d$ values of 15 μM, 9 μM, and 9 μM respectively (FIG. 4A and FIGS. 13A and 13B).

While DLS indicated that 19 and 24 form colloidal aggregates at a concentration of 100 μM, 22 did not show any aggregation at this concentration (FIGS. 9A-G). Lineweaver-Burk analysis indicated 22 is a competitive inhibitor with $K_i$ of 7 μM (FIG. 4C), which is in accordance with the FP assay results for the compound.

Figure 14:
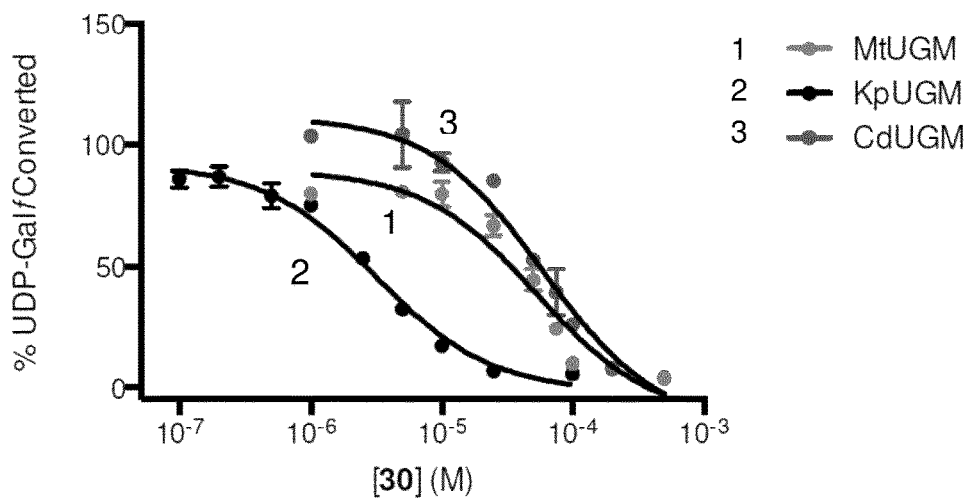
FIG. 14 is a graph illustrating that exemplary compound 30 is selective for KpUGM over MtUGM and CdUGM.

The specificity of in vitro UGM inhibition was assessed using purified recombinant UGM homologs. MtUGM and *C. diptheriae* UGM (CdUGM) share about 43% sequence identity with KpUGM, and 76% identity with each other. However, active site residues are highly conserved between the homologs. Interestingly, 22 showed much lower inhibition towards MtUGM (19% at 100 μM) than KpUGM. Yet, inhibition of CdUGM (38% at 100 μM) by 22 proved slightly better than for MtUGM. This trend was consistent for other analogs from this series (FIG. 14). The fact that these compounds are more potent inhibitors of KpUGM may be a consequence of performing the docking screen with a KpUGM structure.

To gain insight for scaffold optimization, the binding mode of inhibitors from this series by co-crystallization of UGM and 22 was studied. Attempts at co-crystallizing KpUGM with 22 resulted in crystals that diffracted, but twinning prevented the structure from being solved. However, it was possible to solve the crystal structure of CdUGM in complex with 22 to 2.7 Å resolution (not shown) (Table 1). This structure is the first co-crystal structure of UGM in complex with a small molecule inhibitor.

CdUGM crystallized in an open conformation, in contrast to the closed conformation KpUGM structure used for the virtual screen. Compound 22 indeed binds in the active site (not shown). The carboxylate of the inhibitor forms a salt bridge with Arg289, a residue essential for UGM activity [Sanders, D. A. R., et al., UDP-galactopyranose mutase has a novel structure and mechanism. Nat Struct Mol Biol, 2001: p. 1-6]. The $R_1$ thiophene of 22 binds in a hydrophobic pocket formed by Tyr327, Tyr365, Trp163 and Pro328. The $R_2$ chlorophenyl moiety of the inhibitor stacks on top of Tyr327 and π-stacks against Trp163. The co-crystal structure suggests the chlorine atom of 22 may form a halogen bond with the side chain hydroxyl of Ser216.

Overlay of the new crystal structure with the KpUGM structure used for docking results in a clash of 22 with Arg174. This essential residue is located on the flexible loop and thus moves into the UGM active site in the active, reduced form of the enzyme. It is possible that this arginine could adopt a different rotamer to accommodate 22 upon lid closure. The predicted docking pose of 6 places it in the same binding pocket and predicts salt bridge formation with Arg289. However, the overall binding modes of the ligands are quite different due to the opposing conformations of the flexible loop (not shown).

The structure of the complex can also explain some of the SAR witnessed in this series (FIG. 6). Specifically, larger para substitutions on the $R_2$ phenyl ring perform better: pCl-Phe (21)>pMe-Phe (25)>pF-Phe (16)>Phe (6). pCl-Phe performs especially well, compare 21 with 6, possibly due to the potential halogen bond. Thiophene $R_2$ also improved inhibition (20). From the $R_1$ side, bigger moieties performed better: e.g. 19>18>6>17; 24>25; 22>26>21. The placement of $R_1$ in the structure indeed allows for much larger moieties.

Figure 4B:
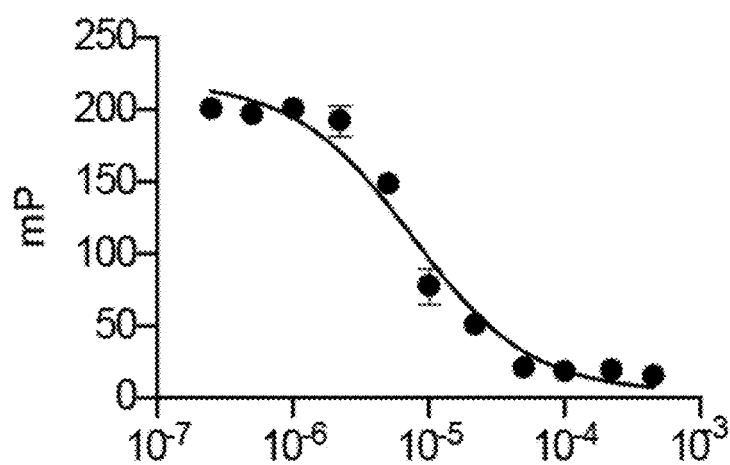
Figure 4C:
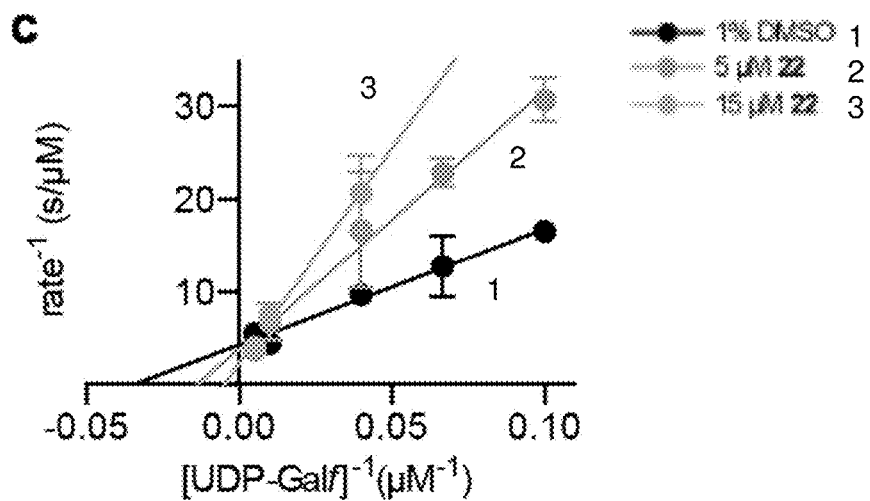
Figure 4D:
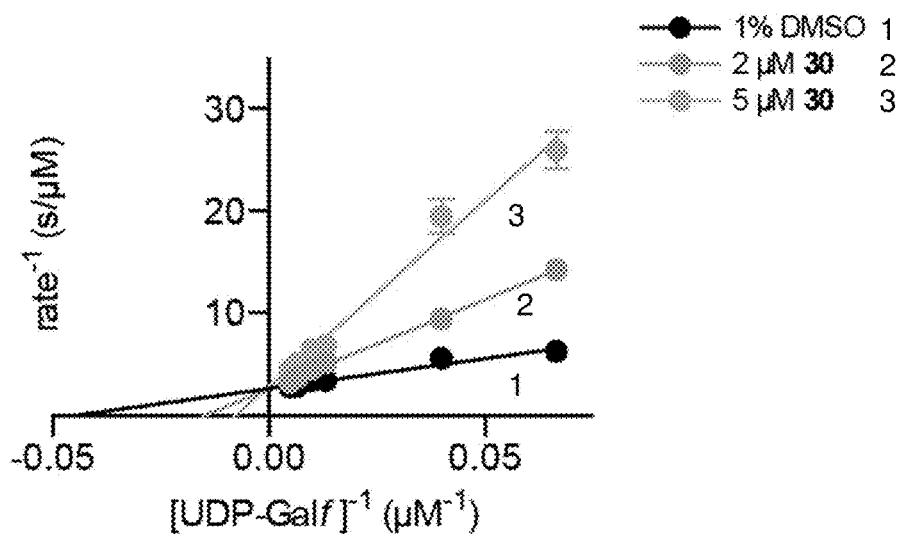
Figure 4E:
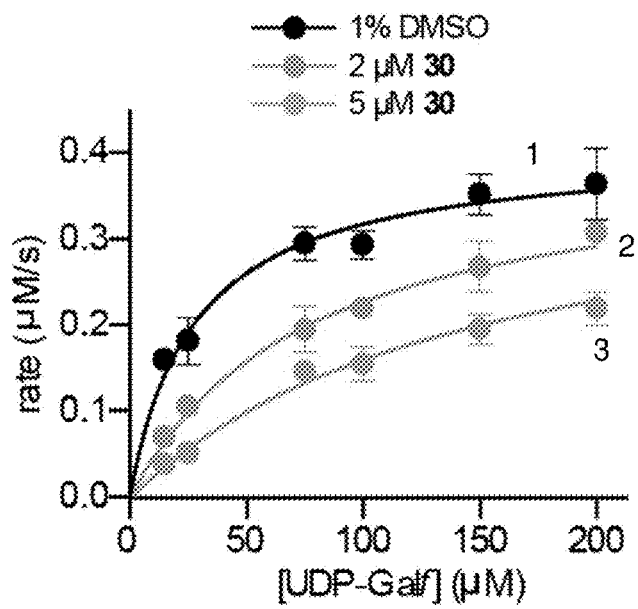
Figure 4F:
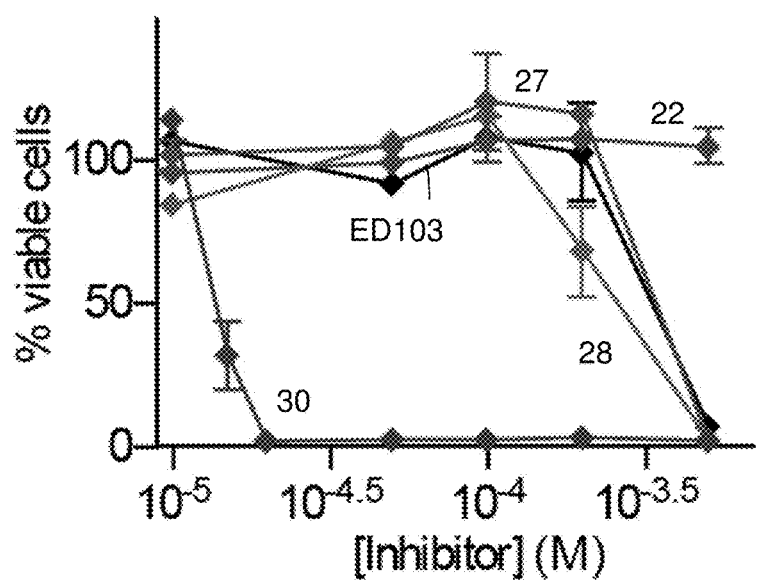

It should be noted that this SAR is based on UGM inhibition of the small molecules at 100 μM, a concentration at which some compounds from this series might be prone to colloid formation (FIGS. 9A-G). Nonetheless, five additional commercially available "second generation" analogs were selected and tested based on this SAR that combine favorable $R_1$ and $R_2$ side chains (FIG. 6). All second generation analogs showed more than 90% inhibition of KpUGM at 100 μM, with three of the five showing more than 90% inhibition at 50 μM. The best inhibitor (30) showed no measurable activity of KpUGM at either of these two concentrations (FIG. 6). Compound 30 was further characterized by Lineweaver-Burk analysis as well as in the FP assay (FIGS. 4B and 4D). Both assays indicated that 30 is a competitive inhibitor of UGM, displaying a $K_i$ and $K_d$ of 1.1 μM and 4.5 μM, respectively.

Figure 9A:
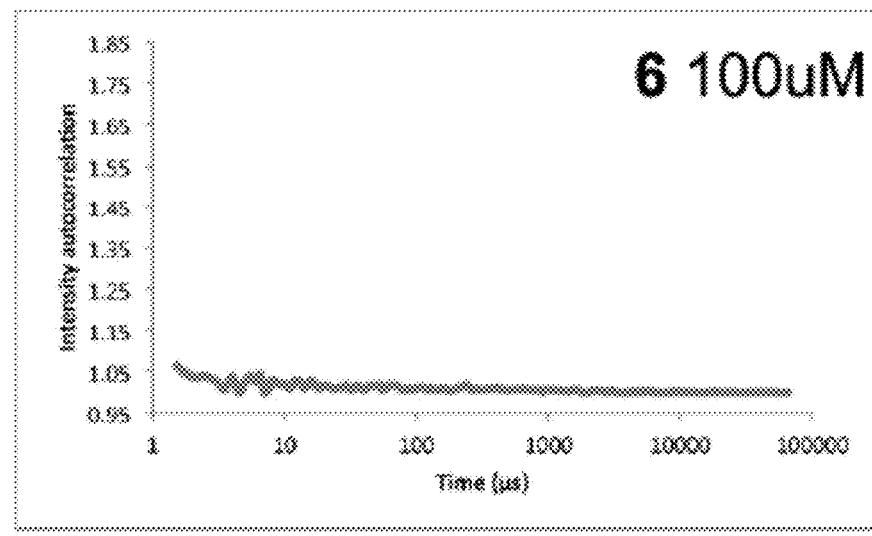
FIGS. 9A-9G include graphs (for the six compounds indicated) related to detection of colloid formers via DLS. DLS auto-correlation plots. Compounds 6, 10 and 22 (FIGS. 9A, 9B, 9D) show no sign of colloidal aggregation via DLS at 100 µM. Compounds 19, 24 and 30 (FIGS. 9C, 9E, 9F) do form colloids at 100 µM. Compound 30, however, does not aggregate at 10 µM (FIG. 9G). Where available, the second curve in a graph represents a replicate of the experiment.
Figure 9B:
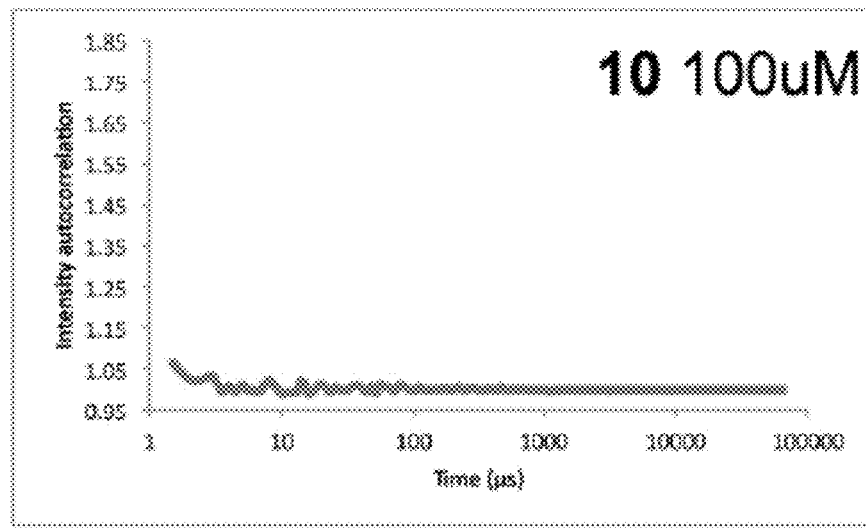
Figure 9C:
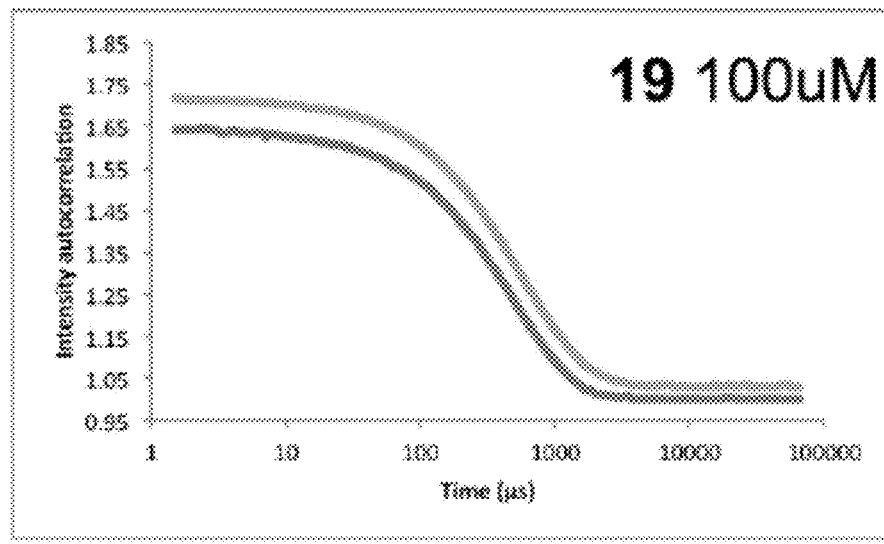
Figure 9D:
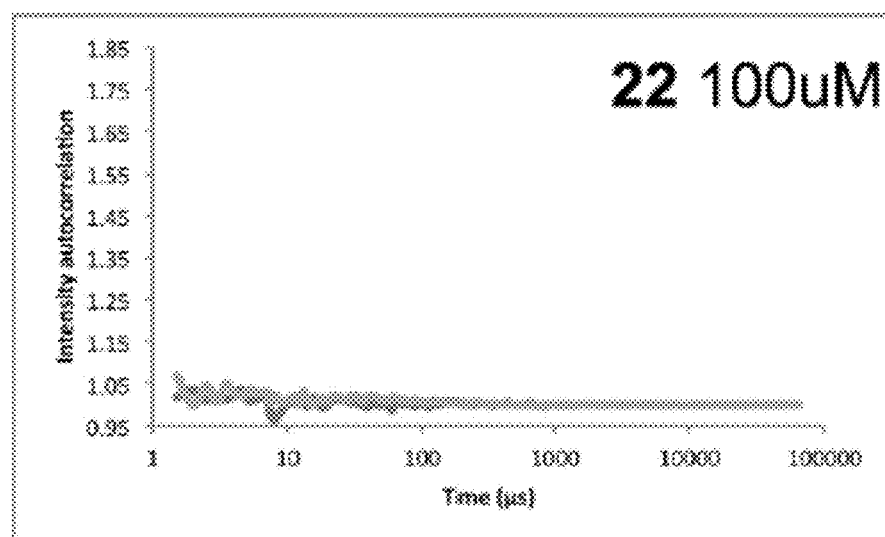
Figure 9E:
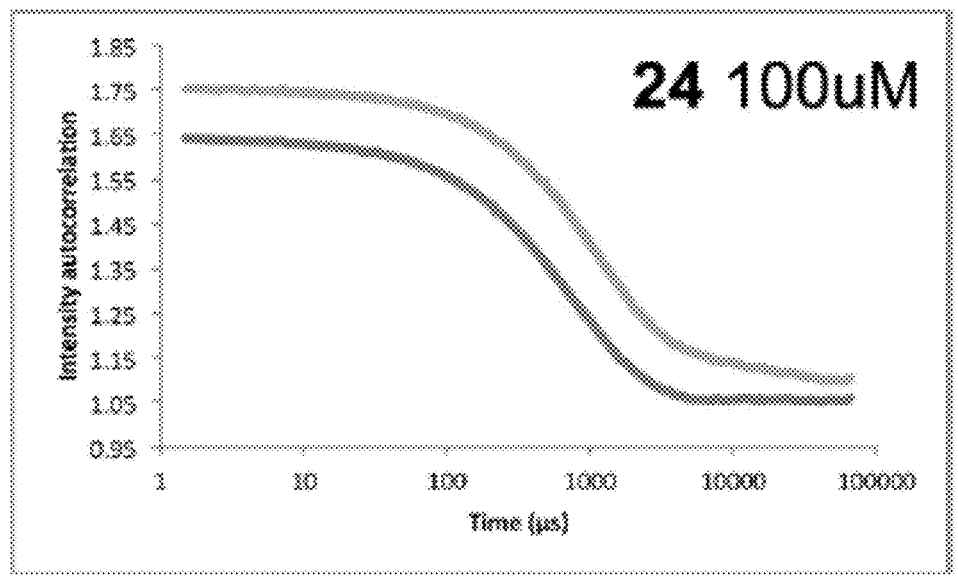
Figure 9F:
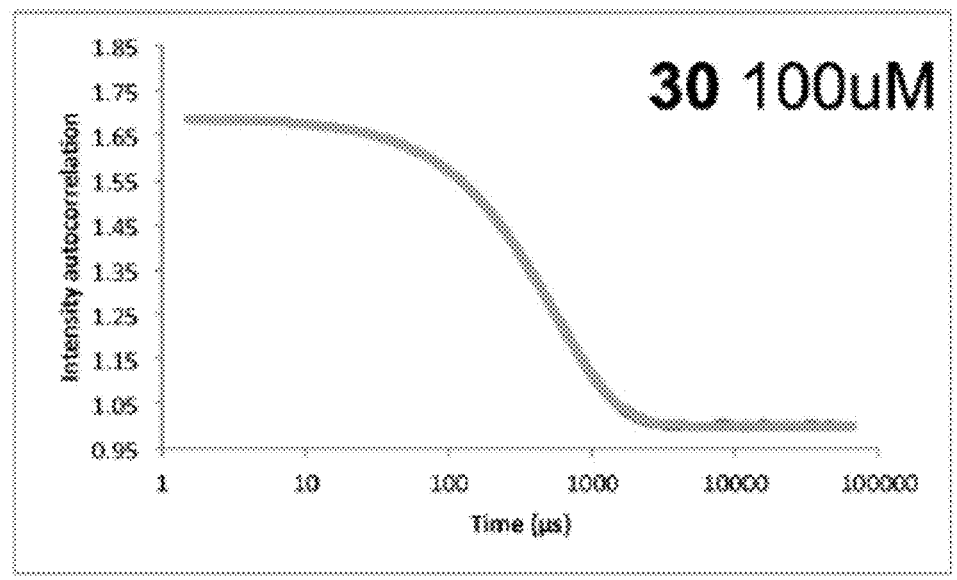
Figure 9G:
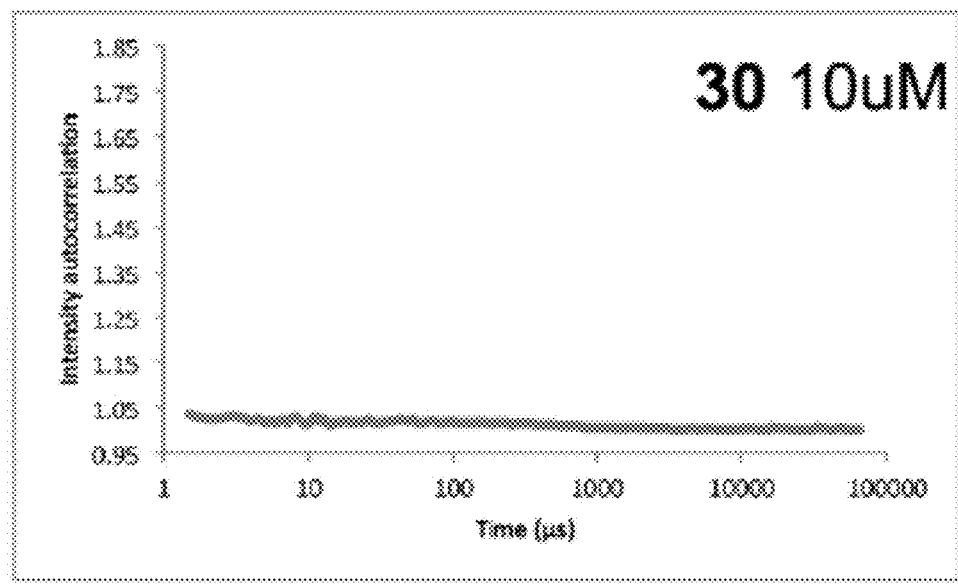
Figure 10A:
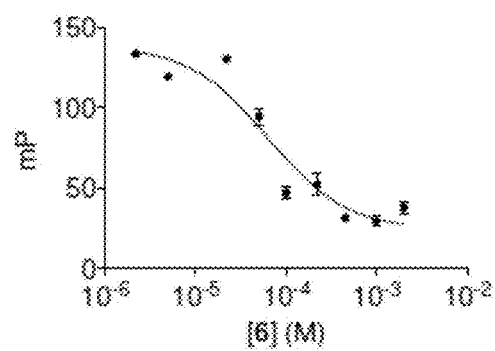
FIGS. 10A and 10B show graphs with characterization of docking for predicted UGM inhibitors 6 and 10 by FP assay. Compounds 6 (FIG. 10A) and 10 (FIG. 10B) displayed Kd values of 43 and 6 µM, respectively.
Figure 10B:
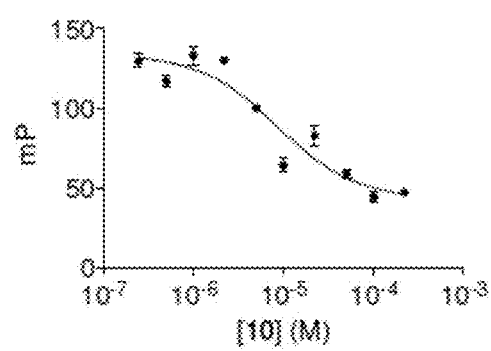
Figure 15:
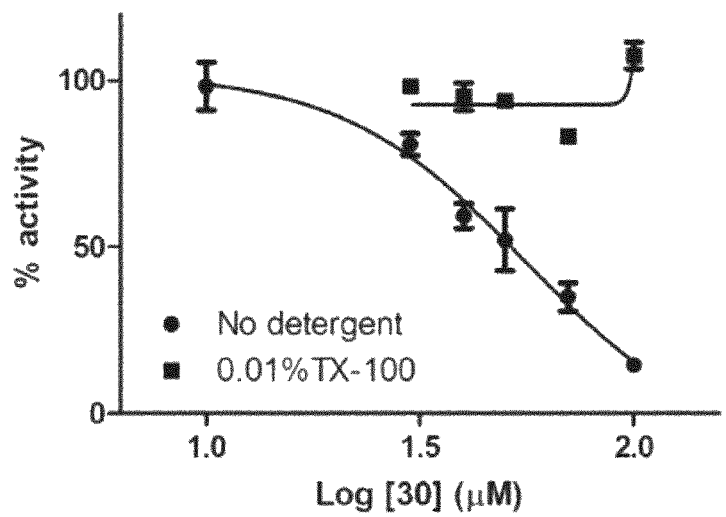
FIG. 15 is a graph showing non-specific MDH inhibition by compound 30. Compound 30 shows non-specific inhibition of MDH with IC50=55.7 µM. This inhibition is reversible by the addition of detergent, a hallmark of colloidal aggregation.
Figure 16:
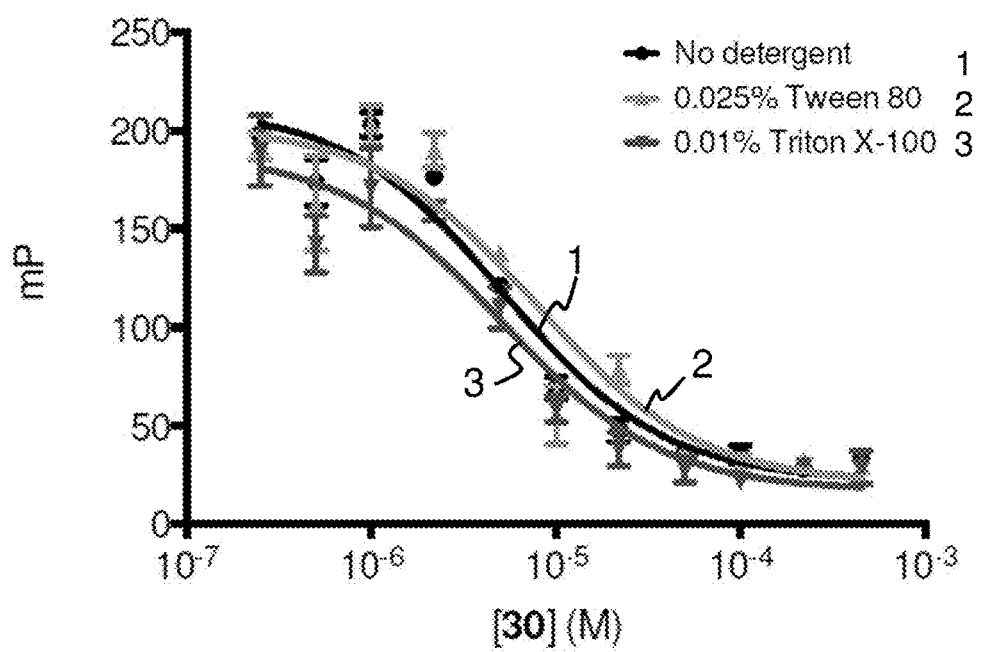
FIG. 16 is a graph showing binding of compound 30 to KpUGM was insensitive to detergent. The FP assay was used to show that the Kd of 30 is unaffected by the presence of detergent. This indicates that KpUGM binding is specific, and not an artifact of small molecule aggregation.

Similar to 19 and 24, compound 30 forms colloidal aggregates at 100 μM (FIG. 9F). Indeed, 30 showed non-specific inhibition of the unrelated enzymes AmpC and malate dehydrogenase (MDH) at high concentrations. However, the critical aggregation concentration of 30, as determined by a full dose response curve for MDH inhibition ($IC_{50}$=55.7 µM; FIG. 15), is significantly higher than its $K_i$ for KpUGM. While MDH inhibition was fully rescued by the addition of detergent, competitive binding of 30 to UGM in the FP assay proved insensitive to detergent (FIG. 16). Taken together with the Lineweaver-Burk analysis, we conclude that UGM inhibition by 30 is competitive specific and not mediated by colloids.

Encouraged by the in vitro properties of molecules from this series, antibacterial activity was assessed via two cell-based approaches: disk diffusion and broth microdilution assays. Growth curves of *Mycobacterium smegmatis*, a fast-growing and nonpathogenic model for *M. tuberculosis*, were generated in liquid media with varied concentrations of our most promising UGM inhibitors. Trends in growth inhibition of *M. smegmatis* aligned well with the measured in vitro properties of our series (FIGS. 4A-4E, FIG. 5). The minimal inhibitory concentration (MIC) of 30 for *M. smegmatis* was determined to be 20 µM. Compound 30 showed no significant cell-killing with control bacterial strains that do not possess a UGM ortholog, such as *B. subtilis*. (MIC=500 µM) and B strain *E. coli* (MIC>500 µM).

Figure 5:
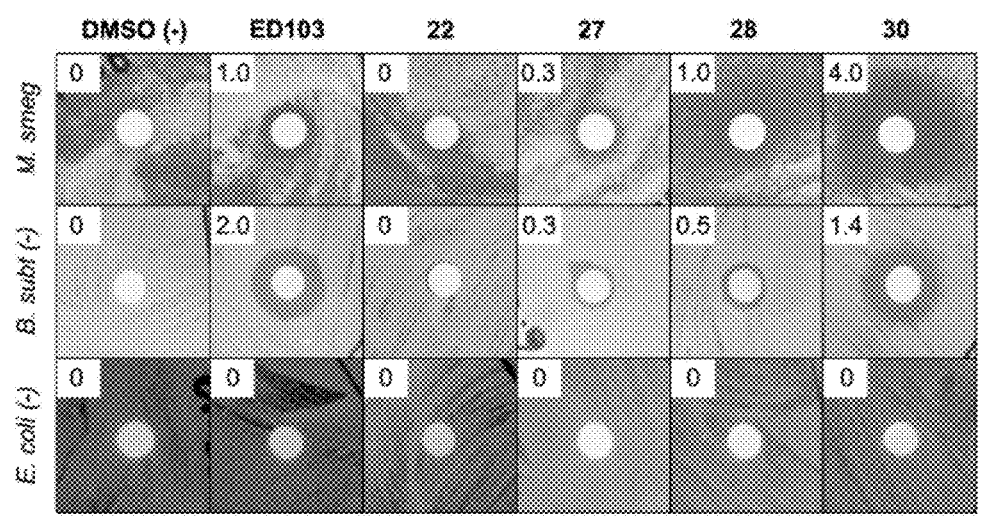
FIG. 5 is a composite of the results of multiple disk diffusion assays showing that UGM inhibitors display antimycobacterial activity in a disk diffusion assay. Compounds 22, 27, 28, and 30 were tested for antibacterial activity against three bacterial strains. UGM is essential for viability of *M. smegmatis*, while *E. coli* (Gram-negative) and *B. subtilis* (Gram-positive) do not contain a UGM. The latter bacterial strains were thus controls to evaluate inhibitor specificity and toxicity. A DMSO vehicle control is shown, as well as UGM inhibitor, ED103. The radius of the growth inhibition zone (measured from outer edge of paper disk to the border of cell growth) is indicated in mm in the upper left corner. The most potent new UGM inhibitor displays better antimycobacterial activity and less off-target effects than ED103.
Figure 6A:
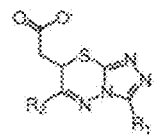
FIGS. 6A-6B is a Table relating to hit-to-lead optimization of compound 6. Analogs of 6 with varied $R_1$ and $R_2$ substituents (structures shown) were evaluated in SAR studies. KpUGM inhibition at 100 and 50 µM was assessed for each compound.
Figure 6B:
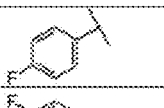
Figure 6B:
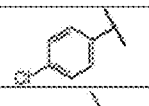
Figure 6B:
Figure 6B:
Figure 6B:
Figure 6B:
Figure 6B:
Figure 6B:
Figure 6B:
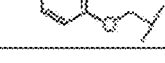
Figure 6B:
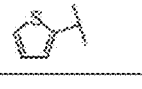
Figure 7A:
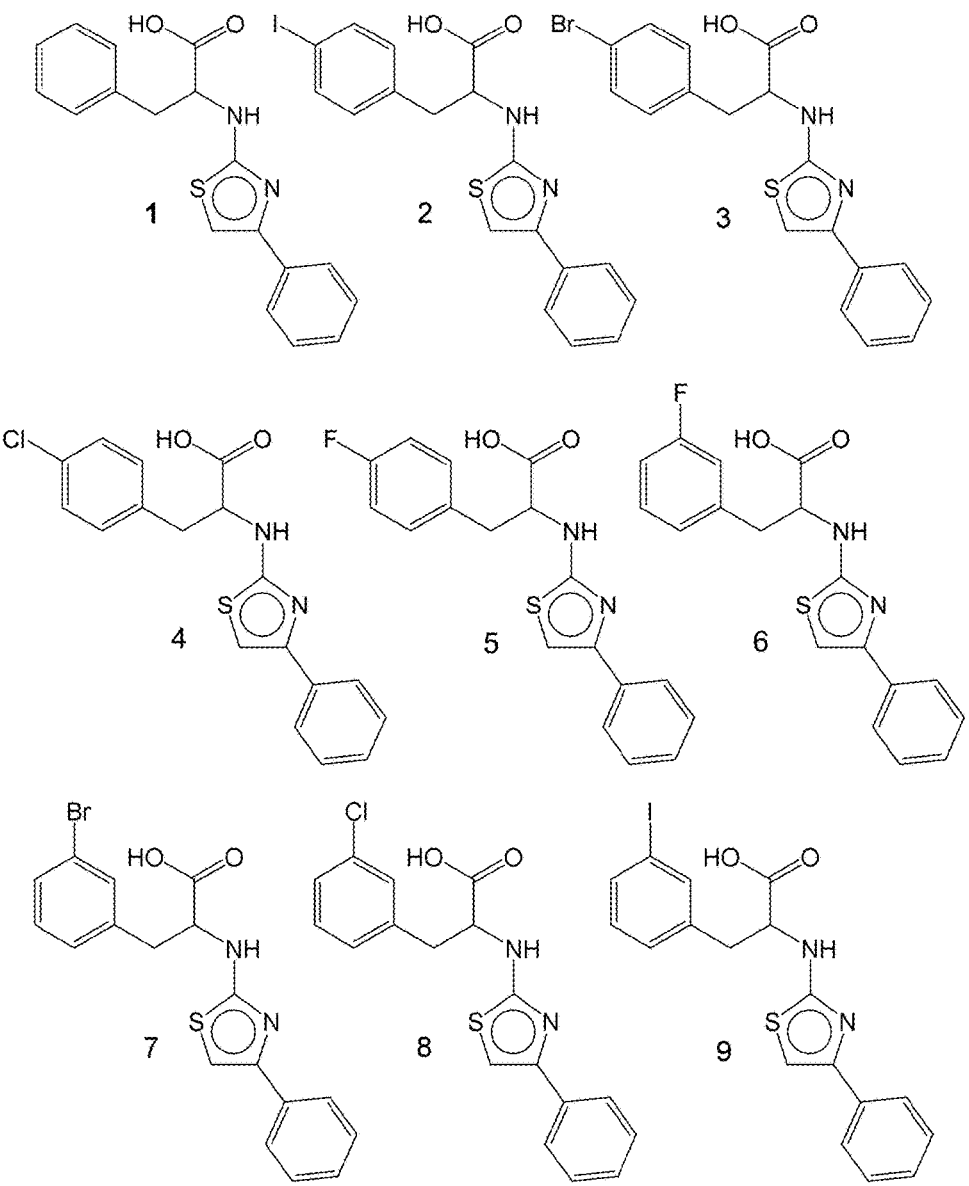
FIGS. 7A-7D shows structures of known UGM inhibitors used for docking calibration. The shown UGM inhibitors have been characterized in previous studies, and were utilized as a training set for our virtual screen.
Figure 7B:
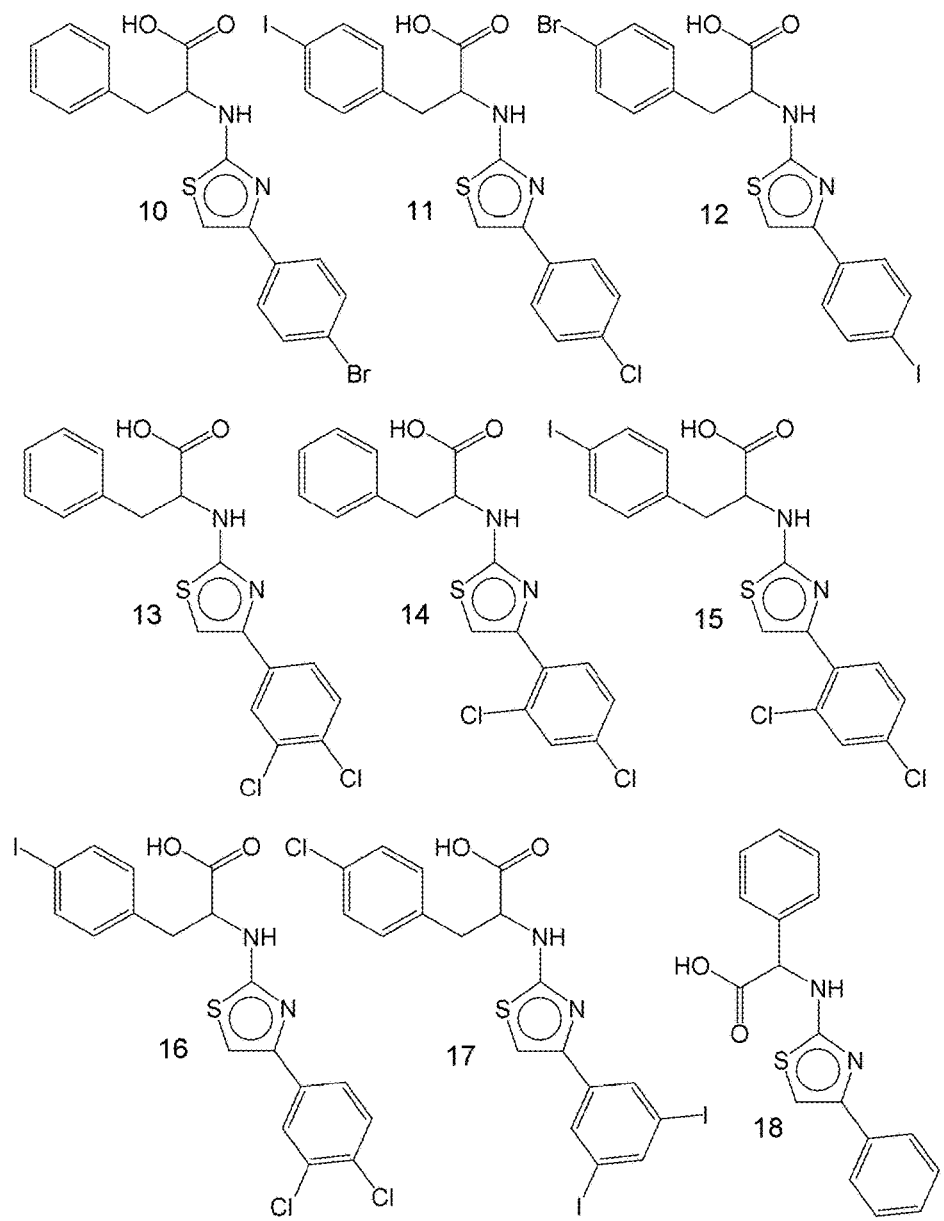
Figure 7C:
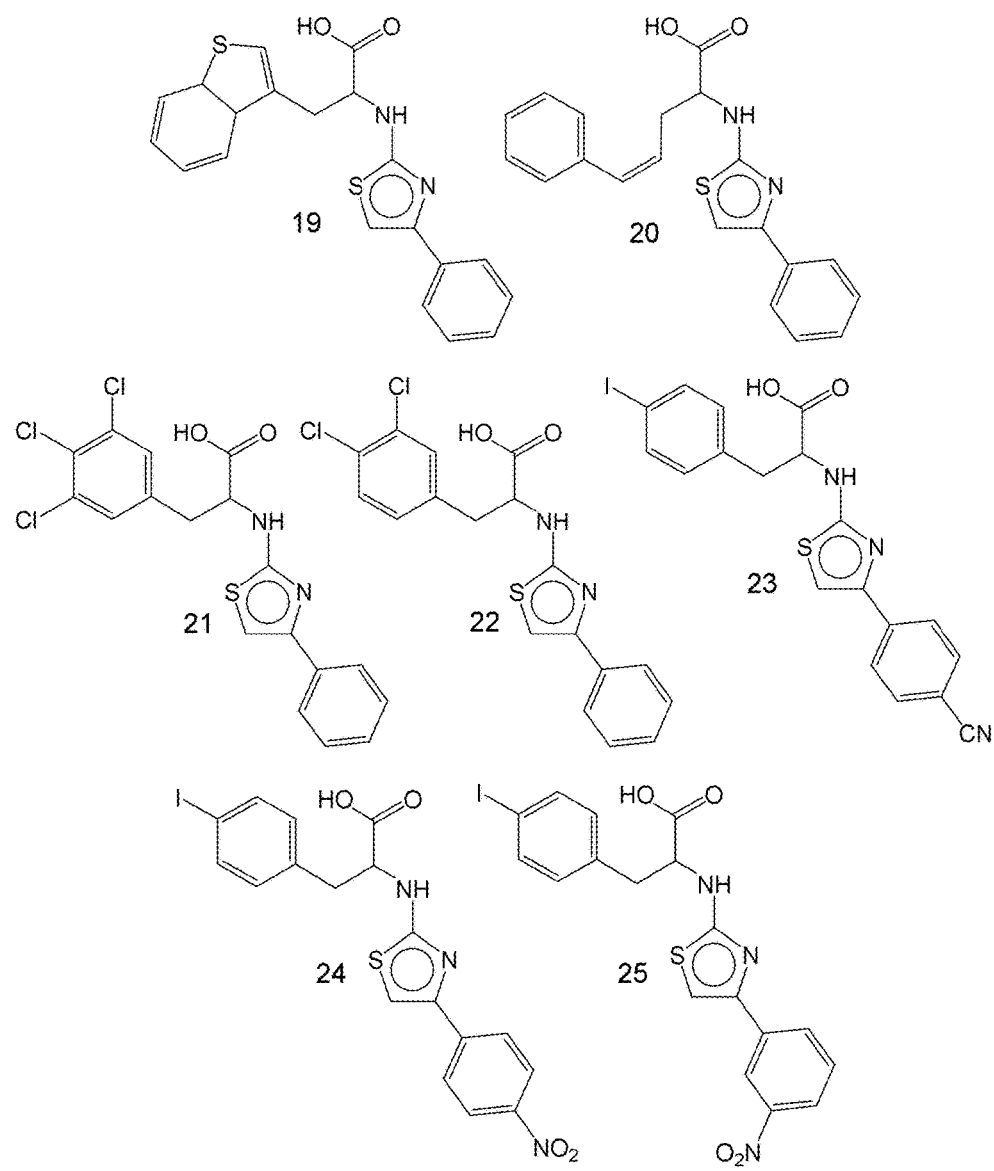
Figure 7D:
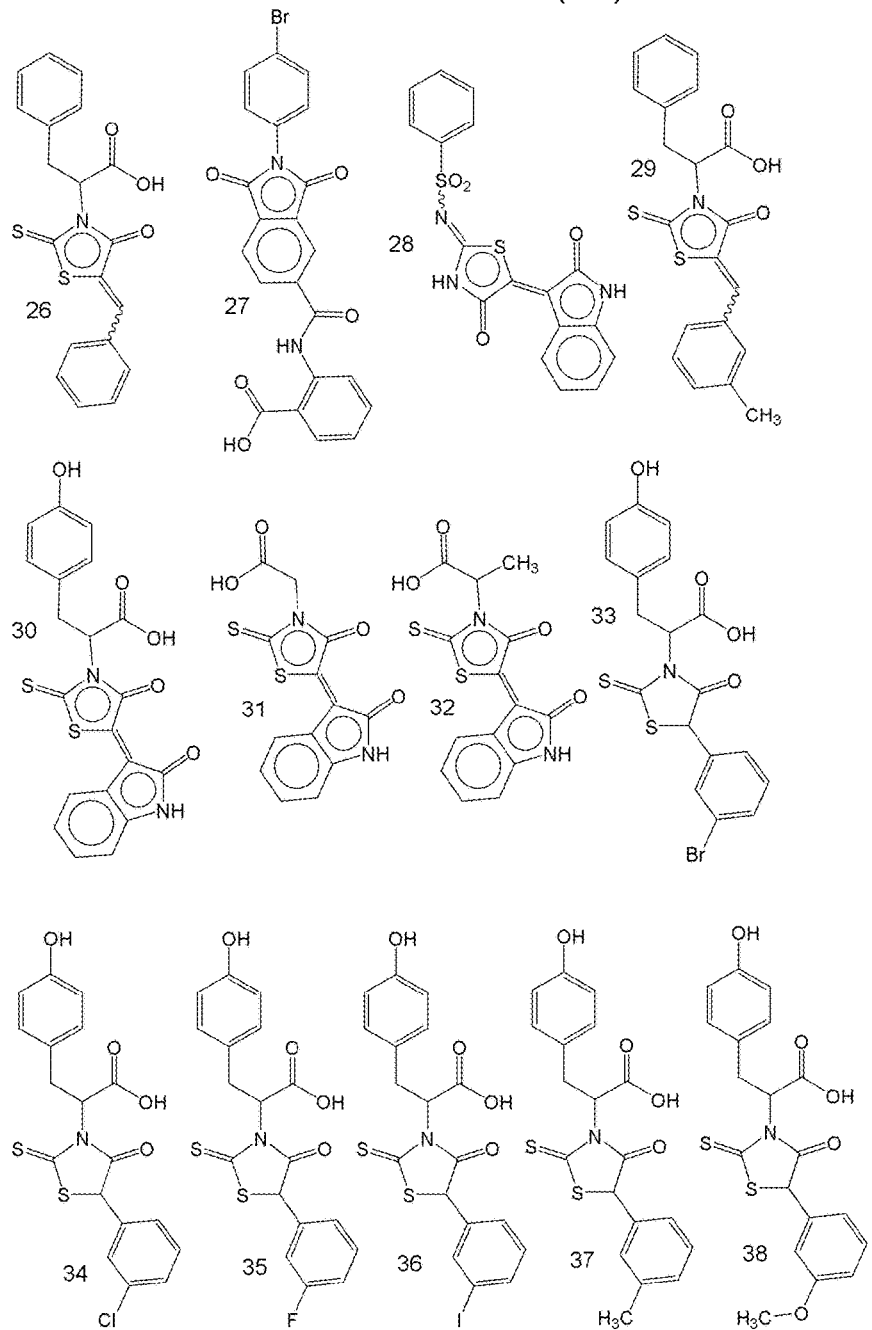

Similar results were obtained in a disk diffusion assay conducted on solid media (FIG. 5). In this experiment, a zone of growth inhibition around a treated disk was measured. Again, compound 30 outperformed all other compounds of the series. Though *B. subtilis* growth inhibition was seen with 30, the zone of inhibition was significantly smaller than that observed for *M. smegmatis*. No cell-killing of *E. coli* occurred at the tested concentration.

Figure 17:
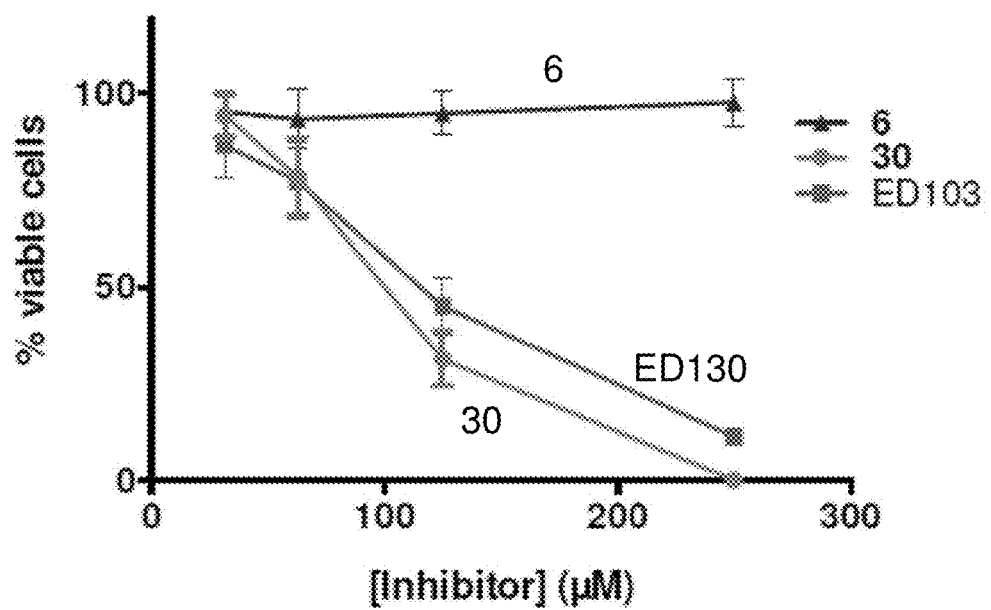
FIG. 17 illustrates cytotoxicity of 30 with HEK293 cells. Compound 30 toxicity to human cells is comparable to the previously described UGM inhibitor ED103 with and LD50~100 µM. The parent compound, 6, displays no significant cellular toxicity.

Additionally, the cytotoxicity of example inhibitor compound 30 with HEK293 cells (FIG. 17) was assessed. Compound 30 was found to be only mildly toxic ($LD_{50}$~100 µM) relative to its MIC for *M. smegmatis* (5-fold difference), leaving a wide therapeutic window.

This work demonstrates that virtual screening is an effective method for identifying small molecule ligands of proteins that have proven challenging in biochemical, target-based HTS. The work provides the first crystal structure of a UGM-inhibitor complex, which may inform future inhibitor design and shed light on specificity determinants of UGM inhibition. The work identified and characterized compounds (Formula I and II) with potent antimycobacterial activity and attractive features for future optimization.

Docking can be a complementary tool to HTS. Regardless of whether the same [Ferreira et al. 2010; Brenk, R., J. J. Irwin, and B. K. Shoichet, Here be dragons: docking and screening in an uncharted region of chemical space. J Biomol Screen, 2005. 10(7): p. 667-74] or different [Doman, T. N., et al., Molecular docking and high-throughput screening for novel inhibitors of protein tyrosine phosphatase-1B. J Med Chem, 2002. 45(11): p. 2213-21] libraries are being screened, docking tends to have higher hit rates and produce chemically novel hits. This study reinforces these observed trends. Several HTS campaigns were performed against Kp and MtUGM, screening close to 400,000 molecules in total (PubChem [Wang, Y., et al., PubChem: a public information system for analyzing bioactivities of small molecules. Nucleic Acids Res, 2009. 37(Web Server issue): p. W623-33] AID: 504406). These endeavors resulted in only a few hits, some of which are uridine analogs [Soltero-Higgin et al. 2004, Scherman, M. S., et al., Drug targeting *Mycobacterium tuberculosis* cell wall synthesis: development of a microtiter plate-based screen for UDP-galactopyranose mutase and identification of an inhibitor from a uridine-based library. Antimicrob Agents Chemother, 2003. 47(1): p. 378-82] and others, namely the TZ series of molecules, are known frequent hitters in HTS [Baell et al. 2010]. Interestingly, compounds 3 and 24 were included in a compound library screened against MtUGM, but they were not detected by HTS. This highlights a major downfall of HTS: false negatives and assay dependence. In the FP assay used for these HTS, displacement of a substrate analog probe gives a read out, limiting the assay to identifying only competitive inhibitors of UGM. Further characterization of 3 may reveal the compound acts on UGM via a different mode of inhibition, explaining why it did not appear as a hit in previous HTS. Compound 24, on the other hand, may have been overlooked by the stringency of HTS. The HTS containing 24 was run against MtUGM. Our results with this series suggest that KpUGM is easier to inhibit than MtUGM (inhibitors are about an order of magnitude more potent against KpUGM in vitro). Thus, 24 may have shown up in previous HTS had KpUGM been the target, or had the defined hit parameters been relaxed. Virtual screening bypassed these HTS shortcomings by allowing more thorough characterization of a much smaller set of candidates.

Virtual screening and docking, of course, have their own caveats. Though UGM possesses a flexible loop as a vital part of its active site, docking only utilizes a single static conformation of the target for screening. HTS, in a sense, targets all protein conformations at once. The determined CdUGM co-crystal structure displays the flexible loop in a radically different conformation than the docking target, underscoring the need for specific consideration of this loop during virtual screening. Utilizing our CdUGM structure to seed future UGM docking screens may enable discovery of different classes of UGM inhibitors.

The newly determined CdUGM structure is a major advancement on several fronts. It is the first crystal structure of UGM from *C. diphtheria*, adding to the small number of available bacterial UGM structures from pathogenic species. Moreover, it is the first structure of UGM in complex with a small molecule inhibitor. The structure helps explain SAR in our inhibitor series and will be instrumental in propelling future optimization. As discussed previously, the observed conformation of CdUGM underscores the importance of the flexible loop (CdUGM residues 169-181). While the UGM active site is highly conserved across bacterial species, some variability exists in the flexible loop region. Different conformations of the loop may be stabilized by sequence elements distal to the binding site of our compounds. This could account for the preferential binding of our inhibitors to distinct UGM orthologs. The dynamics and conformational preferences of this loop warrant further investigation.

While the experimentally determined binding mode of 22 differs from the docking prediction, it remains to be seen which binding mode holds true for KpUGM. Indeed, re-docking of 22 to the CdUGM co-crystal structure closely recapitulates its binding mode. However, this should not hinder the fact that we now have in hand a novel and promising starting point for optimization of a specific antimycobacterial chemotype. Compound 30 is chemically different than any known MtUGM inhibitor in ChEMBL, [Gaulton, A., et al., ChEMBL: a large-scale bioactivity database for drug discovery. Nucleic Acids Res, 2012. 40(Database issue): p. D1100-7] with a chemical similarity score (Tanimoto-coefficient using ECFP4)≤0.16 as well as from any known ligand used in our training set (Tc≤0.24).

Furthermore, the series identified offer straightforward synthetic chemical routes for medicinal chemistry optimization. Derivatives of our scaffold are accessible via combinations of commercially available building blocks having different $R_1$ and $R_2$ or different $R_6$ and $R_7$. In addition to facile synthesis, several features make this series particularly appealing. These include stable SAR, and correspondence between in vitro inhibition and antimycobacterial activity, suggesting efficient cell permeability. Taken together, these features represent marked improvements over earlier UGM inhibitors [Dykhuizen et al 2008], some of which may suffer from off-target effects and toxicity issues [Borrelli et al. 2010].

An interesting characteristic of this series is its aggregation properties. DLS shows that several molecules from the series (e.g. the original docking hit 6 and 22) do not aggregate at concentrations up to 100 µM. Other analogs such as 19, 24 and 30 show aggregation at high concentrations (FIGS. 9A-9G); however, non-specific enzyme inhibition assays and detergent controls (FIGS. 8, 9A-9G, 15 and 16) verified that the UGM inhibition observed for the molecules prone to colloidal formation was achieved at concentrations below their critical aggregation concentration. This property should be kept in mind in future optimization of this chemotype. In fact, in some scenarios small molecule aggregation might provide beneficial pharmacokinetics [Owen, S. C., et al., Colloidal aggregation affects the efficacy of anticancer drugs in cell culture. ACS Chem Biol, 2012. 7(8): p. 1429-35].

Molecular docking was performed with DOCK 3.6 with scoring including rapid context-dependent ligand desolvation using the solvent-excluded volume method as described in [Mysinger et al. 2010], DelPhi [Gilson, M. K. and B. Honig, Calculation of the total electrostatic energy of a macromolecular system: solvation energies, binding energies, and conformational analysis. Proteins, 1988. 4(1): p. 7-18] based electrostatics and a thin layer of electrostatic spheres as described in [Mysinger, M. M., et al., Structure-based ligand discovery for the protein-protein interface of chemokine receptor CXCR4. Proc Natl Acad Sci USA, 2012. 109(14):5517-22]. Sampling parameters were varied and assess by enrichment of known ligands over decoys as described in the results including the following: (final parameters are bolded). distance_tolerance=1.5, 2.0, 2.3, 2.5, 3.0(Å); ligand_binsize/receptor_binsize 0.2, 0.3, 0.4, 0.5, 1.0(Å); ligand_overlap/receptor_overlap 0.1, 0.4, 0.5, 0.6, 0.7, 1.0, 1.5(Å). 45 matching spheres were used based on the crystallographic ligand. Final energies were computed after 250 steps of rigid-body minimization.

A single rotamer change was introduced to PDB 3INT chain B based on a minimization of the predicted DOCK pose of a known ligand (#14 in Supplementary FIG. 1) using RosettaLigand [Davis, I. W. and D. Baker, RosettaLigand docking with full ligand and receptor flexibility. J Mol Biol, 2009. 385(2): p. 381-92] Rosetta command line: ligand_dock.static.linuxgccrelease-s complex.pdb-database <database>-extra_res_fa lig.params-nstruct 10-ligand:minimize_ligand-ligand:harmonic_torsions 10-ligand:soft_rep-ligand:old_estat-packing::ex1-packing::ex1aro-packing::ex2-packing::extrachi_cutoff 1

The docking property matched decoys were generated by the DUD-E server[Mysinger, M. M., et al, 2012].

Fifty decoys were generated for each of the 38 ligands described in FIG. 7. For the final virtual screen, ZINC's [Irwin et al. 2012] pre-generated lead-like subset (subset 1) was docked containing 4.7 million molecules at the time.

Selection of Candidates for Testing.

The top 500 molecules from the virtual screen were filtered via Marvin (ChemAxon, Budapest, Hungary) to assess correct protonation state of the molecules. SMARTS filter calculation was performed through the Smartsfilter web application, Division of Biocomputing, Dept. of Biochem & Mol Biology, University of New Mexico, Albuquerque, N. Mex., (web site pangolin.health.unm.edu/tomcat/biocomp/smartsfilter) to remove potential reactive molecules or frequent non-specific hitters [Baell et al. 2010]. The rest of the molecules were scrutinized manually by visual inspection to assess characteristics orthogonal to the scoring function such as overly strained conformations, and simple availability from vendors. Compound similarity was calculated using ECFP4-based Tanimoto coefficients [Rogers, D. and M. Hahn, Extended-connectivity fingerprints. J Chem Inf Model, 2010. 50(5): p. 742-54.] as implemented in Pipeline-Pilot [Pilot, P., version 6.1; SciTegic Inc.: San Diego, Calif. 92123-1365].

Dynamic Light Scattering.

To evaluate aggregation by DLS compounds were diluted from concentrated stocks in DMSO into filtered 50 mM potassium phosphate, pH 7.0. The final DMSO concentration was 1%, and compound concentrations were usually 100 µM. Samples were run in duplicates. All measurements were made at room temperature using a DynaPro MS/X (Wyatt Technology) with a 55 mW laser at 826.6 nm. The laser power was 100%, and the detector angle was 90°.

Aggregation Counter Screens.

Compounds were tested for inhibition of Malate Dehydrogenase and AmpC β-lactamase as reported. Assays were performed in 50 mM potassium phosphate buffer, pH 7.0 at 25° C. For AmpC the molecules were mixed with buffer and CENTA substrate (50 µM; Tydock Pharma; Modena, Italy) to a final concentration of 1% DMSO (v/v). Reactions were initiated by addition of β-Lactamase (1 nM). Change in absorbance was monitored at 405 nm for 3 minutes. For Malate Dehydrogenase assay (MDH; Sigma Cat# M-7032), the molecule was mixed with buffer and 2 nM final concentration of the enzyme to a final concentration of 1% DMSO (v/v) and were incubated for five minutes. MDH reactions were started by adding substrates: Oxaloacetic acid (20 mM stock in buffer, prepared fresh daily; Sigma Cat# O4126) to a final concentration 200 µM and NADH (20 mM stock in buffer—prepare fresh daily; Sigma Cat# N-4505) to a final concentration 200 µM. Change in absorbance was monitored at 410 nm for 2.5 minutes. Absorbance was monitored on an HP 8453 UV—visible spectrophotometer (Agilent, Technologies, Santa Clara, Calif.). The assays were performed in duplicate in methacrylate disposable cuvettes.

Compound Sources.

Compounds were sourced from the following vendors: compounds 1, 5, 12, 13 from Chembridge, compounds 3,4 from Pharmeks, compounds 8,11 from Vitas-M laboratory, 2,6,7,9,10 and 14-31 from Enamine. All compounds were sourced at 95% or greater purity as described by the vendors.

Recombinant Protein Expression and Purification.

KpUGM and MtbUGM were recombinantly expressed and purified as previously described with slight modifications [Carlson et al. 2006; Gruber, T. D., et al., Ligand Binding and Substrate Discrimination by UDP-Galactopyranose Mutase. J Mol Biol, 2009. 391(2): p. 327-340]. Briefly, E. coli BL21(DE3) cells containing KpUGM-pGEMEasy or MtUGM-pET-29b constructs were grown in LB with 100 µg/ml ampicillin or 50 µg/ml kanamycin. When cells reached mid-log phase, recombinant protein expression was induced with 0.1 mM IPTG and cells were grown overnight at 15° C. Cells were harvested and lysed as before, and the His-tagged proteins were purified via Ni-affinity chromatography on an ÄKTA FPLC (Amersham Biosciences) [Carlson et al. 2006; Gruber et al. 2009]. Protein aliquots were vitrified in liquid nitrogen and stored at −80° C.

Open reading frame coding for residue 18-404 of CdUGM was amplified from genomic DNA of *C. diphtheriae* NCTC 13129 (ATCC). The PCR product was cloned into a modified pMALc5× vector, resulting in a N-terminally His-tagged UGM with a TEV cleavage site. The expression plasmid was transformed into *Escherichia coli* ER2523 and expression was induced with 0.1 mM IPTG at 15° C. when the optical density reached 0.6. Protein was purified as previously described for KpUGM [Beis, K., et al., Crystal Structures of Mycobacteria tuberculosis and *Klebsiella pneumoniae* UDP-Galactopyranose Mutase in the Oxidised State and *Klebsiella pneumoniae* UDP-Galactopyranose Mutase in the (Active) Reduced State. J Mol Biol, 2005. 348(4): p. 971-982].

Crystallography.

Purified CdUGM was extensively dialyzed against 20 mM Tris-HCl (pH 7) and concentrated to 10 mg/mL. The concentration of protein was based on FAD content measured as absorbance at 450 nm using an extinction coefficient of 11300 $M^{-1}$ $cm^{-1}$. Compound 22 (50 mM stock in DMSO) was added to achieve final concentration of 5 mM 22 and 9 mg/mL CdUGM. Hanging drop vapor diffusion was performed by mixing 2 μL of protein solution and 2 μL of well solution (100 mM Bis-Tris (pH 6.5), 2 M ammonium sulfate), and equilibrating against 500 μL of the well solution. Crystals appeared and grew to full size within 2 weeks. The crystals were cryoprotected by briefly swipping through 100 mM Bis-Tris (pH 6.5), 2.5 M ammonium sulfate, and 15% glycerol, and then vitrified and stored in liquid nitrogen. Single crystal diffraction data was collected at beamline X25 at National Synchrotron Light Source, Brookhaven National Laboratory. Data reduction and scaling were performed with HKL2000 (Table 1) [Otwinowski, Z. and W. Minor, Processing of x-ray diffraction data collected in oscillation mode, in Methods in enzymology: macromolecular crystallography, part A, J. C. W. Carter and R. M. Sweet, Editors. 1997, Academic Press New York. p. 307-326]. Molecular replacement was performed with PHENIX AutoMR [Adams, P. D., et al., PHENIX: a comprehensive Python-based system for macromolecular structure solution. Acta Crystallogr D Biol Crystallogr, 2010. 66: p. 213-22139; McCoy, A. J., et al., Phaser crystallographic software. J Appl Crystallogr, 2007. 40: p. 658-674] using a previously reported *Escherichia coli* UGM structure (PDB ID: 1I8T) [Sander et al. 2001] as a search model. FAD and 22 coordinates and restraints were generated using eLBOW [Moriarty, N., R. Grosse-Kunstleve, and P. Adams, Electronic Ligand Builder and Optimization Workbench (eLBOW): a tool for ligand coordinate and restraint generation. Acta Crystallogr D Biol Crystallogr, 2009. 65: p. 1074-1080]. Model adjustment and refinement were performed in Coot [Emsley, P., et al., Features and development of Coot. Acta Crystallogr D Biol Crystallogr, 2010. 66: p. 486-501] and phenix.refine [Afonine, P. V., R. W. Grosse-Kunstleve, and P. D. Adams, The Phenix refinement framework. CCP4 Newsl, 2005. 42: p. 8], respectively (Table 1). The model was validated using MolProbity [Chen, V. B., et al., MolProbity: all-atom structure validation for macromolecular crystallography. Acta Crystallogr D Biol Crystallogr, 2010. 66: p. 12-21]. Crystal structure figures were generated with PyMOL [DeLano, W. L., The PyMOL molecular graphics system. 2002].

UGM In Vitro Inhibition.

Enzymatic activity of recombinant UGM was monitored using an HPLC-based assay [Wesener et al., 2013; Lee et al. 1996; Zhang, Q. and H.-w. Liu, Studies of UDP-Galactopyranose Mutase from *Escherichia coli*: An Unusual Role of Reduced FAD in Its Catalysis. J. Amer. Chem. Soc., 2000. 122(38): p. 9065-9070]. Reactions were performed in duplicate at 22° C. in 50 mM NaH2PO4 buffer (pH 7) with 20 nM enzyme and 20 mM fresh sodium dithionite. Small molecules were added from DMSO stocks to a final concentration of 1% DMSO. Concentration of UDP-Galf [Marlow, A. L. and L. L. Kiessling, Improved Chemical Synthesis of UDP-Galactofuranose. Org Lett, 2001. 3(16): p. 2517-2519] was held constant at the Km of the UGM homolog being analyzed, except for generation of Lineweaver-Burk plots. Reaction time and substrate concentration were varied for Lineweaver-Burk analysis, and each condition was tested in triplicate. Quenched reactions were run through a CarboPac PA-100 column (Thermo Scientific) on an Agilent 1260 Infinity HPLC using an isocratic elution of 200 mM ammonium acetate (pH 8) to separate substrate and product peaks.

Small Molecule Binding to UGM.

A fluorescence polarization assay was used to measure ligand binding to KpUGM [Soltero-Higgin et al. 2004, Carlson et al. 2006] Tumbling of the fluorescein-UDP conjugated probe was measured on a Tecan M1000 microplate reader, exciting with 470 nm light and monitoring emission at 525 nm. Each condition was tested in triplicate in the presence of 220 nM KpUGM and 23.3 nM of the probe. Data was fit with a one-site binding nonlinear regression in GraphPad Prism 6.

Microbroth Dilution Assay.

A starter culture of *M. smegmatis* $mc^2155$ (ATCC 700084) was grown to saturation at 30° C. in Middlebrook 7H9 Broth with Albumin Dextrose Catalase (ADC) enrichment and 0.05% Tween 80. Small molecules or DMSO (vehicle control) were added to wells of a sterile 96-well plate. Cells were diluted 200× ($OD_{600}$~0.03) into fresh 7H9 Middlebrook media with 0.05% Tween 80 and added to the plate, yielding a final DMSO concentration of 1% in each well. After 46 hours of growth in a 30° C. shaking incubator, cell viability was measured using an alamar Blue assay (Invitrogen).

Disk Diffusion Assay.

Saturated starter cultures of *E. coli* B121(DE3), *B. subtilis* (OI 1878) [Ying, C. W. and G. W. Ordal, Nucleotide sequence and expression of cheF, an essential gene for chemotaxis in Bacillus subtilis. J Bacteriol, 1989. 171(3): p. 1-8], and *M. smegmatis* were grown, the former two species in LB broth and the later in 7H9 Middlebrook media. Cells were diluted to an $OD_{600}$ of 0.2 in fresh media and spread (100 μL) onto LB agar plates. Following an hour of incubation at 37° C., sterile cloning disks (3.2 mm diameter, Scienceware) impregnated with 100 nmol of compound or 2 μL of DMSO were placed on the surface of the inoculated solid media. Cells were incubated at 37° C. overnight. Plates with *M. smegmatis* were incubated 3 additional days at room temperature. Zones of inhibition were measured from the outer edge of the cloning disk to the border of cell growth.

Cytotoxicity Assay.

Four thousand HEK 293T cells were added to wells of a sterile 96-well plate in 99 μl DMEM with 10% FBS. The plate was incubated for 24 hours at 37° C. with 5% $CO_2$ to allow cells to attach. Cells were then treated with serially diluted small molecules or a vehicle control. The final DMSO concentration was 1% in each well. After 24 hours of incubation, viability of the treated cells was analyzed using CellTiter-Glo Luminescent Cell Viability Assay (Promega). Viability readings were normalized to DMSO control wells.

TABLE 1

| X-ray Data collection Statistics | |
|---|---|
| Wavelength (Å) | 1.1 |
| Resolution range (Å) | 42.2-2.70 (2.80-2.70) |
| Space group | P 64 2 2 |
| Unit cell | 179.4 179.4 145.2 90 90 120 |
| Total reflections | 370592 |
| Unique reflections | 37906 |
| Multiplicity | 9.8 (9.8) |
| Completeness (%) | 99.2 (98.7) |
| Mean I/sigma(I) | 20.0 (3.8) |
| Wilson B-factor | 73.64 |
| R-sym | 0.074 (0.642) |
| R-meas | 0.078 (0.677) |
| R-pim | 0.025 (0.214) |
| Refinement Statistics | |
| Resolution range (Å) | 42.2-2.7 (2.77-2.70) |
| R-factor | 0.1847 (0.2906) |
| R-free (5%) | 0.2334 (0.3953) |
| Number of atoms | 6633 |
| macromolecules | 6372 |
| ligands | 166 |
| water | 95 |
| Protein residues | 772 |
| RMS(bonds) | 0.008 |
| RMS(angles) | 1.23 |
| Ramachandran favored (%) | 95 |
| Ramachandran outliers (%) | 0.78 |
| Clashscore | 11.83 |
| Average B-factor | 59.50 |
| macromolecules | 59.20 |
| ligands | 77.35 |
| solvent | 48.00 |

Statistics for the highest-resolution shell are shown in parentheses.

SCHEME 1

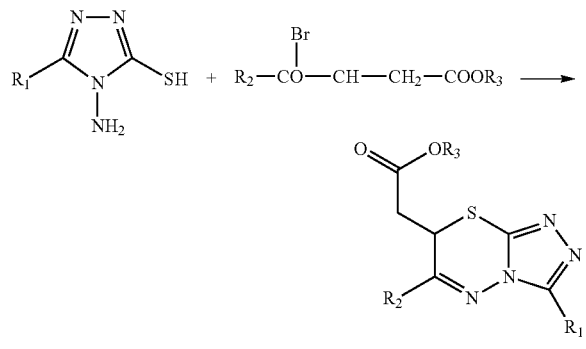

See: Dhindsa and Vaid (1986) Indian J. Chem. Vol. 25B pp 283-287

SCHEME 2

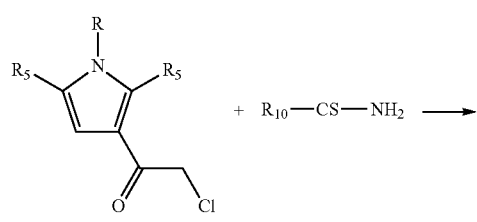

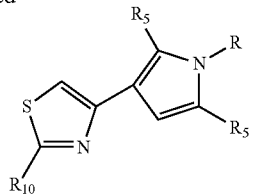

where R can be —$(CH_2)p$-CO-Y and Y can include an appropriate protecting group See: Vovk, M. et al. (2010) Molecules 15:997-1006

REFERENCES

1. Richards, M. R. and T. L. Lowary, *Chemistry and Biology of Galactofuranose-Containing Polysaccharides*. Chem Bio Chem, 2009. 10(12): p. 1920-1938.
2. Tefsen, B., et al., *Galactofuranose in eukaryotes: aspects of biosynthesis and functional impact*. Glycobiology, 2012. 22(4): p. 456-469.
3. Wesener, D. A., et al., *UDP-galactopyranose mutase in nematodes*. Biochemistry, 2013. 52(25): p. 4391-8.
4. Pan, F., et al., *Cell Wall Core Galactofuran Synthesis Is Essential for Growth of Mycobacteria*. J Bacteriol, 2001. 183(13): p. 3991-3998.
5. Soltero-Higgin, M., et al., *A unique catalytic mechanism for UDP-galactopyranose mutase*. Nat Struct Mol Biol, 2004. 11(6): p. 539-543.
6. Dykhuizen, E. C., et al., *Inhibitors of UDP-galactopyranose mutase thwart mycobacterial growth*. J Am Chem Soc, 2008. 130(21): p. 6706-7.
7. Borrelli, S., et al., *Antimycobacterial activity of UDP-galactopyranose mutase inhibitors*. Intl Antimicrob Agents, 2010. 36(4): p. 364-8.
8. Soltero-Higgin, M., et al., *Identification of inhibitors for UDP-galactopyranose mutase*. J Am Chem Soc, 2004. 126(34): p. 10532-3.
9. Dykhuizen, E. C. and L. L. Kiessling, *Potent ligands for prokaryotic UDP-galactopyranose mutase that exploit an enzyme subsite*. Org Lett, 2009. 11(1): p. 193-6.
10. Carlson, E. E., J. F. May, and L. L. Kiessling, *Chemical probes of UDP-galactopyranose mutase*. Chem Biol, 2006. 13(8): p. 825-37.
11. Shoichet, B. K., *Virtual screening of chemical libraries*. Nature, 2004.432(7019): p. 862-5.
12. Ferreira, R. S., et al., *Complementarity between a docking and a high-throughput screen in discovering new cruzain inhibitors*. J Med Chem, 2010. 53(13): p. 4891-905.
13. Babaoglu, K., et al., *Comprehensive mechanistic analysis of hits from high-throughput and docking screens against beta-lactamase*. J Med Chem, 2008. 51(8): p. 2502-11.
14. Lorber, D. M. and B. K. Shoichet, *Hierarchical docking of databases of multiple ligand conformations*. Curr Top Med Chem, 2005. 5(8): p. 739-49.
15. Mysinger, M. M. and B. K. Shoichet, *Rapid context-dependent ligand desolvation in molecular docking*. J Chem Inf Model, 2010. 50(9): p. 1561-73.
16. Gruber, T. D., et al., *X-ray crystallography reveals a reduced substrate complex of UDP-galactopyranose mutase poised for covalent catalysis by flavin*. Biochemistry, 2009. 48(39): p. 9171-3.

17. Mysinger, M. M., et al., *Directory of useful decoys, enhanced (DUD-E): better ligands and decoys for better benchmarking.* J Med Chem, 2012. 55(14): p. 6582-94.
18. Baell, J. B. and G. A. Holloway, *New substructure filters for removal of pan assay interference compounds (PAINS) from screening libraries and for their exclusion in bioassays.* J Med Chem, 2010. 53(7): p. 2719-40.
19. Teague, S. J., et al., *The Design of Leadlike Combinatorial Libraries.* Angew Chem Int Ed Engl, 1999. 38(24): p. 3743-3748.
20. Irwin, J. J., et al., *ZINC: a free tool to discover chemistry for biology.* J Chem Inf Model, 2012. 52(7): p. 1757-68.
21. Chad, J. M., et al., *Site-directed mutagenesis of UDP-galactopyranose mutase reveals a critical role for the active-site, conserved arginine residues.* Biochemistry, 2007. 46(23): p. 6723-32.
22. Lee, R., et al., *Enzymatic Synthesis of UDP-Galactofuranose and an Assay for UDP-Galactopyranose Mutase Based on High-Performance Liquid Chromatography.* Anal Biochem, 1996: p. 1-7.
23. McGovern, S. L., et al., *A common mechanism underlying promiscuous inhibitors from virtual and high-throughput screening.* J Med Chem, 2002. 45(8): p. 1712-22.
24. Sanders, D. A. R., et al., *UDP-galactopyranose mutase has a novel structure and mechanism.* Nat Struct Mol Biol, 2001: p. 1-6.
25. Brenk, R., J. J. Irwin, and B. K. Shoichet, *Here be dragons: docking and screening in an uncharted region of chemical space.* J Biomol Screen, 2005. 10(7): p. 667-74.
26. Doman, T. N., et al., *Molecular docking and high-throughput screening for novel inhibitors of protein tyrosine phosphatase-1B.* J Med Chem, 2002. 45(11): p. 2213-21.
27. Wang, Y., et al., *PubChem: a public information system for analyzing bioactivities of small molecules.* Nucleic Acids Res, 2009. 37(Web Server issue): p. W623-33.
28. Scherman, M. S., et al., *Drug targeting Mycobacterium tuberculosis cell wall synthesis: development of a microtiter plate-based screen for UDP-galactopyranose mutase and identification of an inhibitor from a uridine-based library.* Antimicrob Agents Chemother, 2003. 47(1): p. 378-82.
29. Gaulton, A., et al., *ChEMBL: a large-scale bioactivity database for drug discovery.* Nucleic Acids Res, 2012. 40(Database issue): p. D1100-7.
30. Owen, S. C., et al., *Colloidal aggregation affects the efficacy of anticancer drugs in cell culture.* ACS Chem Biol, 2012. 7(8): p. 1429-35.
31. Gilson, M. K. and B. Honig, *Calculation of the total electrostatic energy of a macromolecular system: solvation energies, binding energies, and conformational analysis.* Proteins, 1988. 4(1): p. 7-18.
32. Mysinger, M. M., et al., *Structure-based ligand discovery for the protein-protein interface of chemokine receptor CXCR4.* Proc Natl Acad Sci USA, 2012. 109(14): p. 5517-22.
33. Davis, I. W. and D. Baker, *RosettaLigand docking with full ligand and receptor flexibility.* J Mol Biol, 2009. 385(2): p. 381-92.
34. Rogers, D. and M. Hahn, *Extended-connectivity fingerprints.* J Chem Inf Model, 2010. 50(5): p. 742-54.
35. Pilot, P., version 6.1; SciTegic Inc.: San Diego, Calif. 92123-1365.
36. Gruber, T. D., et al., *Ligand Binding and Substrate Discrimination by UDP-Galactopyranose Mutase.* J Mol Biol, 2009. 391(2): p. 327-340.
37. Beis, K., et al., *Crystal Structures of Mycobacteria tuberculosis and Klebsiella pneumoniae UDP-Galactopyranose Mutase in the Oxidised State and Klebsiella pneumoniae UDP-Galactopyranose Mutase in the (Active) Reduced State.* J Mol Biol, 2005. 348(4): p. 971-982.
38. Otwinowski, Z. and W. Minor, *Processing of x-ray diffraction data collected in oscillation mode*, in *Methods in enzymology: macromolecular crystallography, part A*, J. C. W. Carter and R. M. Sweet, Editors. 1997, Academic Press New York. p. 307-326.
39. Adams, P. D., et al., *PHENIX: a comprehensive Python-based system for macromolecular structure solution.* Acta Crystallogr D Biol Crystallogr, 2010. 66: p. 213-221.
40. McCoy, A. J., et al., *Phaser crystallographic software.* J Appl Crystallogr, 2007. 40: p. 658-674.
41. Moriarty, N., R. Grosse-Kunstleve, and P. Adams, *Electronic Ligand Builder and Optimization Workbench (eLBOW): a tool for ligand coordinate and restraint generation.* Acta Crystallogr D Biol Crystallogr, 2009. 65: p. 1074-1080.
42. Emsley, P., et al., *Features and development of Coot.* Acta Crystallogr D Biol Crystallogr, 2010. 66: p. 486-501.
43. Afonine, P. V., R. W. Grosse-Kunstleve, and P. D. Adams, *The Phenix refinement framework.* CCP4 Newsl, 2005. 42: p. 8.
44. Chen, V. B., et al., *MolProbity: all-atom structure validation for macromolecular crystallography.* Acta Crystallogr D Biol Crystallogr, 2010. 66: p. 12-21.
45. DeLano, W. L., *The PyMOL molecular graphics system.* 2002.
46. Zhang, Q. and H.-w. Liu, *Studies of UDP-Galactopyranose Mutase from Escherichia coli: An Unusual Role of Reduced FAD in Its Catalysis.* Journal of the American Chemical Society, 2000. 122(38): p. 9065-9070.
47. Marlow, A. L. and L. L. Kiessling, *Improved Chemical Synthesis of UDP-Galactofuranose.* Org Lett, 2001. 3(16): p. 2517-2519.
48. Ying, C. W. and G. W. Ordal, *Nucleotide sequence and expression of cheF, an essential gene for chemotaxis in Bacillus subtilis.* J Bacteriol, 1989. 171(3): p. 1-8.

The invention claimed is:

1. A method for inhibiting uridine 5'-diphosphate-galactopyranose mutase (UGM) which comprises contacting UGM with an amount of one or more compounds of formula II or salts thereof effective for inhibiting the enzyme wherein formula II is

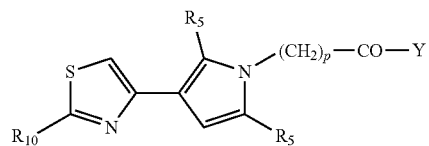

and salts thereof,
where:
Y is —$OR_4$, or —$NH_2$;
p is 1, 2 or 3;
$R_4$ is selected from the group consisting of an alkyl, cycloalkyl, alkenyl, cycloalkenyl, heterocyclyl, aryl or heteroaryl group, each of which groups are optionally substituted, and hydrogen;
each $R_5$ is independently hydrogen or an optionally substituted alkyl group having 1-3 carbon atoms; and
$R_{10}$ is an —$NR_6R_7$ group or hydrogen, where:

$R_6$ and $R_7$ are independently selected from the group consisting of hydrogen, or optionally substituted alkyl, cycloalkyl, alkenyl, cycloalkenyl, heterocyclyl, aryl or heteroaryl groups;

where substitution, if present, is substitution with one or more substituents selected from the group consisting of halogen, nitro, cyano, isocyano, thiocyano, isothiocyano, hydroxyl, $C_1$-$C_6$ alkyl, $C_1$-$C_6$ alkoxy, sulfonamide (—$SO_2$—$N(R_F)_2$), azide, sulfonyl (—$SO_2$—$R_F$), —$COOR_F$, —$COR_F$, —$CON(R_F)_2$, —$N(R_F)_2$, and $C_1$-$C_6$ haloalkyl groups, where $R_F$ is hydrogen or a $C_1$-$C_6$ alkyl group.

2. The method of claim 1, wherein the UGM is that of a *mycobacterium* or a nematode.

3. The method of claim 1, wherein contacting comprises contacting a microorganism having UGM or contacting the environment of the microorganism with the one or more compounds of formula II, or salts thereof.

4. A method for inhibiting the growth of a microorganism which comprises contacting the microorganism or an environment containing the microorganism with an effective amount of one or more compounds formula II or salts thereof as defined herein, wherein
formula II is

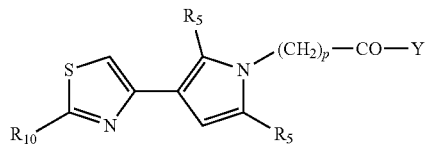

and salts thereof,
where:
Y is —$OR_4$, or —$NH_2$;
p is 1, 2 or 3;
$R_4$ is selected from the group consisting of an alkyl, cycloalkyl, alkenyl, cycloalkenyl, heterocyclyl, aryl or heteroaryl group, each of which groups are optionally substituted, and hydrogen;
each $R_5$ is independently hydrogen or an optionally substituted alkyl group having 1-3 carbon atoms; and
$R_{10}$ is an —$NR_6R_7$ group or hydrogen,
where:
$R_6$ and $R_7$ are independently selected from the group consisting of hydrogen, or optionally substituted alkyl, cycloalkyl, alkenyl, cycloalkenyl, heterocyclyl, aryl or heteroaryl groups;
where substitution, if present, is substitution with one or more substituents selected from the group consisting of halogen, nitro, cyano, isocyano, thiocyano, isothiocyano, hydroxyl, $C_1$-$C_6$ alkyl, $C_1$-$C_6$ alkoxy, sulfonamide (—$SO_2$—$N(R_F)_2$), azide, sulfonyl (—$SO_2$—$R_F$), —$COOR_F$, —$COR_F$, —$CON(R_F)_2$, —$N(R_F)_2$, and $C_1$-$C_6$ haloalkyl groups, where $R_F$ is hydrogen or a $C_1$-$C_6$ alkyl group,
wherein the microorganism is a bacterium, a fungus, an algae or a nematode.

5. The method of claim 4, wherein the microorganism is a *mycobacterium* or a nematode.

6. The method of claim 4, where, in the compound of formula II, Y is OH, both $R_5$ are methyl, $R_{10}$ is —$NR_6R_7$, $R_6$ is hydrogen and $R_7$ is 1-phenylethyl.

7. A method of treating an infection by a microorganism having UGM in an individual in need of such treatment by administering to the individual an effective amount of one or more compounds of formula II or salts thereof, wherein:
formula II is

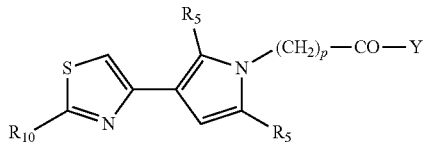

and salts thereof,
where:
Y is —$OR_4$, or —$NH_2$;
p is 1, 2 or 3;
$R_4$ is selected from the group consisting of an alkyl, cycloalkyl, alkenyl, cycloalkenyl, heterocyclyl, aryl or heteroaryl group, each of which groups are optionally substituted, and hydrogen;
each $R_5$ is independently hydrogen or an optionally substituted alkyl group having 1-3 carbon atoms; and
$R_{10}$ is an —$NR_6R_7$ group or hydrogen,
where:
$R_6$ and $R_7$ are independently selected from the group consisting of hydrogen, or optionally substituted alkyl, cycloalkyl, alkenyl, cycloalkenyl, heterocyclyl, aryl or heteroaryl groups;
where substitution, if present, is substitution with one or more substituents selected from the group consisting of halogen, nitro, cyano, isocyano, thiocyano, isothiocyano, hydroxyl, $C_1$-$C_6$ alkyl, $C_1$-$C_6$ alkoxy, sulfonamide (—$SO_2$—$N(R_F)_2$), azide, sulfonyl (—$SO_2$—$R_F$), —$COOR_F$,
—$COR_F$, —$CON(R_F)_2$, —$N(R_F)_2$, and $C_1$-$C_6$ haloalkyl groups, where $R_F$ is hydrogen or a $C_1$-$C_6$ alkyl group,
wherein the microorganism is a bacterium, a fungus, an algae or a nematode.

8. The method of claim 7, wherein the infection is tuberculosis.

9. The method of claim 7, where in the compound of formula II Y is OH, both $R_5$ are methyl, $R_{10}$ is —$NR_6R_7$, $R_6$ is hydrogen and $R_7$ is 1-phenylethyl.

10. A pharmaceutically acceptable composition which comprises one or more compounds of formula II or salts thereof and a pharmaceutically acceptable carrier wherein formula II is

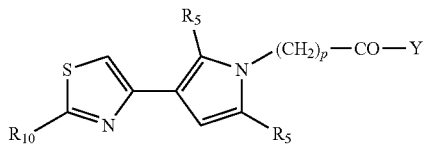

and salts thereof,
where:
Y is —$OR_4$, or —$NH_2$;
p is 1, 2 or 3;
$R_4$ is selected from the group consisting of an alkyl, cycloalkyl, alkenyl, cycloalkenyl, heterocyclyl, aryl and heteroaryl group, each of which groups are optionally substituted, and hydrogen;
each $R_5$ is independently hydrogen or an optionally substituted alkyl group having 1-3 carbon atoms; and
$R_{10}$ is an —$NR_6R_7$ group or hydrogen, where:
R$_6$ and R$_7$ are independently selected from the group consisting of hydrogen, or optionally substituted alkyl, cycloalkyl, alkenyl, cycloalkenyl, heterocyclyl, aryl or heteroaryl groups;
where substitution, if present, is substitution with one or more substituents selected from the group consisting of halogen, nitro, cyano, isocyano, thiocyano, isothiocyano, hydroxyl, C$_1$-C$_6$ alkyl, C$_1$-C$_6$ alkoxy, sulfonamide (—SO$_2$—N(R$_F$)$_2$), azide, sulfonyl (—SO$_2$—R$_F$), —COOR$_F$, —COR$_F$, CON(R$_F$)$_2$, —N(R$_F$)$_2$, and C$_1$-C$_6$ haloalkyl groups, where R$_F$ is hydrogen or a C$_1$-C$_6$ alkyl group, and wherein when R$^4$ is an alkyl group, the alkyl has 6-12 carbon atoms, and with the exception that the compound is not compound 10 of formula:

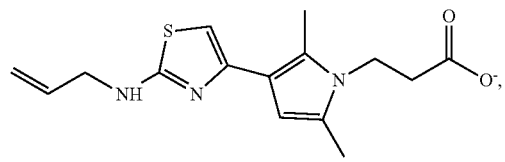

or
compound 14 of formula:

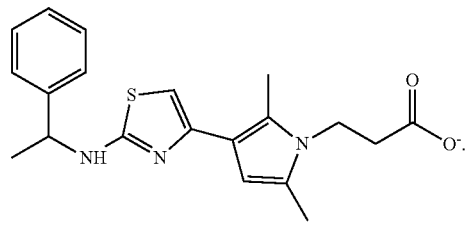

11. A compound of formula II or a salt thereof, wherein formula II is

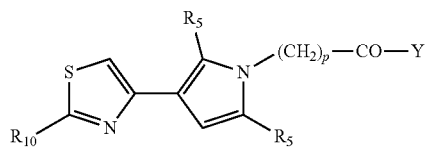

and salts thereof,
where:
Y is —OR$_4$, or —NH$_2$;
p is 1, 2 or 3;
R$_4$ is selected from the group consisting of an alkyl, cycloalkyl, alkenyl, cycloalkenyl, heterocyclyl, aryl or heteroaryl group, each of which groups are optionally substituted, and hydrogen;
each R$_5$ is independently hydrogen or an optionally substituted alkyl group having 1-3 carbon atoms; and
R$_{10}$ is an —NR$_6$R$_7$ group or hydrogen,
where:
R$_6$ and R$_7$ are independently selected from the group consisting of hydrogen, or optionally substituted alkyl, cycloalkyl, alkenyl, cycloalkenyl, heterocyclyl, aryl or heteroaryl groups;
where optional substitution is substitution with one or more substituents selected from the group consisting of halogen, nitro, cyano, isocyano, thiocyano, isothiocyano, hydroxyl, C$_1$-C$_6$ alkyl, C$_1$-C$_6$ alkoxy, sulfonamide (—SO$_2$—N(R$_F$)$_2$), azide, sulfonyl (—SO$_2$—R$_F$), —COOR$_F$, —COR$_F$, —CON(R$_F$)$_2$, —N(R$_F$)$_2$, and C$_1$-C$_6$ haloalkyl groups, where R$_F$ is hydrogen or a C$_1$-C$_6$ alkyl group,
and wherein when R$^4$ is an alkyl group, the alkyl has 6-12 carbon atoms, and with the exception that the compound is not compound 10 of formula:

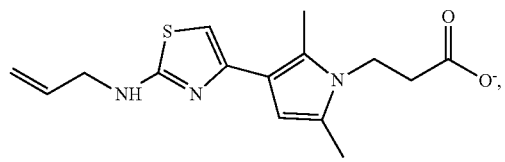

or
compound 14 of formula:

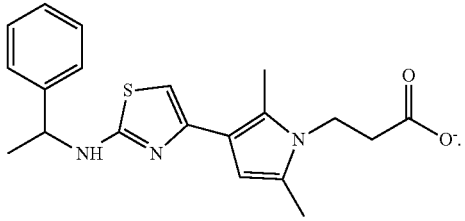

12. A compound or salt thereof of claim 11, where R$_{10}$ is —NR$_6$R$_7$, R$_6$ is hydrogen or methyl and R$_7$ is a substituted phenyl, benzyl or phenethyl group.

13. A compound or salt thereof of claim 12, where the phenyl, benzyl or phenethyl group is substituted with one or more halogen, one or more alkoxy, one or more alkyl, or one or more nitro groups.

14. A compound or salt thereof of claim 12, where the phenyl, benzyl or phenethyl group is substituted with one or more halogen.

15. The method of claim 4, where in the compound of formula II, Y is OH and R$_{10}$ is —NR$_6$R$_7$.

16. The composition of claim 10, where, in the compound of formula II, Y is OH, and R$_{10}$ is —NR$_6$R$_7$.

17. The compound or salt of claim 11, wherein Y is OH and R$_{10}$ is —NR$_6$R$_7$.

18. A compound of formula II:

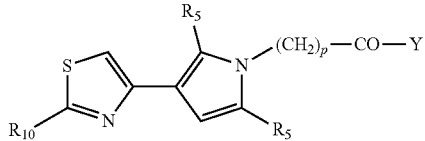

and salts thereof,
wherein Y is OH, both R$_5$ are methyl, R$_{10}$ is —NR$_6$R$_7$, R$_6$ is hydrogen and R$_7$ is 1-phenylethyl.

19. A pharmaceutically acceptable composition which comprises a compound of claim 18 or salts thereof and a pharmaceutically acceptable carrier.

* * * * *